US006612978B2

(12) United States Patent
Lau et al.

(10) Patent No.: US 6,612,978 B2
(45) Date of Patent: Sep. 2, 2003

(54) EXPANDABLE CARDIAC HARNESS FOR TREATING CONGESTIVE HEART FAILURE

(75) Inventors: Lilip Lau, Sunnyvale, CA (US); Bill Hartigan, Fremont, CA (US)

(73) Assignee: Paracor Surgical, Inc., Sunnyvale, CA (US)

( * ) Notice: Subject to any disclaimer, the term of this patent is extended or adjusted under 35 U.S.C. 154(b) by 0 days.

(21) Appl. No.: 09/952,074

(22) Filed: Sep. 10, 2001

(65) Prior Publication Data

US 2002/0045799 A1 Apr. 18, 2002

Related U.S. Application Data

(63) Continuation of application No. 09/634,043, filed on Aug. 8, 2000.
(60) Provisional application No. 60/188,282, filed on Mar. 10, 2000, and provisional application No. 60/171,792, filed on Dec. 22, 1999.

(51) Int. Cl.$^7$ .............................. A61B 19/00; H61F 2/00
(52) U.S. Cl. .......................................................... 600/37
(58) Field of Search ................................ 600/37, 16–18; 128/897, 898; 606/157; 623/66.1, 3; 601/11

(56) References Cited

U.S. PATENT DOCUMENTS

| 2,826,193 A | 3/1958 | Vineberg |
| 3,464,322 A | 9/1969 | Pequignot |
| 3,513,836 A | 5/1970 | Sausse |
| 3,587,567 A | 6/1971 | Schiff |
| 3,613,672 A | 10/1971 | Schiff |
| 3,983,863 A | 10/1976 | Janke et al. |
| 4,048,990 A | 9/1977 | Goetz |
| 4,192,293 A | 3/1980 | Asrican |
| 4,261,342 A | 4/1981 | Aranguren Duo |
| 4,372,293 A | 2/1983 | Vijil-Rosales |
| 4,403,604 A | 9/1983 | Wilkinson et al. |

(List continued on next page.)

FOREIGN PATENT DOCUMENTS

| DE | 38 31 540 A1 | 4/1989 |
| DE | 38 31 540 C2 | 4/1989 |
| DE | 295 17 393 U 1 | 3/1996 |
| DE | WO 98/58598 | 12/1998 |
| EP | 82 09330 | 12/1983 |
| EP | 0280 564 A2 | 8/1988 |
| EP | 0 370 931 A1 | 5/1990 |
| EP | 0 583 012 | 2/1994 |
| FR | 2527435 | 2/1983 |

(List continued on next page.)

OTHER PUBLICATIONS

Alaim Carpentier, M.D., Ph.D., et al, *Dynamic Cardiomyoplasy at Seven Years*, The Journal of Thoracic and Cardiovascular Surgery, vol. 106, No. 1, Dec. 1999.
Eli R. Capouya, M.D., et al., *Girdling Effect of Nonstimulated Cardomyoplasty on left Ventricular Function*, The Society of Thoracic Surgeons, 1993;56:867–71.
O. H. Frazier, M.D. and Timothy J. Myers, BS, *Left Ventricular Assist System as a Bridge to Myocardial Recovery*, The Society of Thoracic Surgeons, 68: 734–41, Dec. 1999.
Joong Hwan Oh, M.D., et al, *Mechanisms of Dynamic Cardomyoplasty: Current Concepts*, J. Card Surg, 1996: 11:194–199, Dec. 1996.

(List continued on next page.)

*Primary Examiner*—Samuel G. Gilbert
(74) *Attorney, Agent, or Firm*—Knobbe, Martens, Olson & Bear, LLP.

(57) ABSTRACT

A cardiac harness for treating congestive heart failure is disclosed. The harness applies elastic, compressive reinforcement on the left ventricle to reduce deleterious wall tension and to resist shape change of the ventricle during the mechanical cardiac cycle. Rather than imposing a dimension beyond which the heart cannot expand, the harness provides no hard limit over the range of diastolic expansion of the ventricle. Instead, the harness follows the contour of the heart throughout diastole and continuously exerts gentle resistance to stretch. Also disclosed is a method of delivering the cardiac harness to the heart minimally invasively.

13 Claims, 32 Drawing Sheets

U.S. PATENT DOCUMENTS

| | | |
|---|---|---|
| 4,428,375 A | 1/1984 | Ellman |
| 4,536,893 A | 8/1985 | Parravicini |
| 4,628,937 A | 12/1986 | Hess et al. |
| 4,630,597 A | 12/1986 | Kantrowitz et al. |
| 4,690,134 A | 9/1987 | Snyders |
| 4,821,723 A | 4/1989 | Baker, Jr. et al. |
| 4,827,932 A | 5/1989 | Ideker et al. |
| 4,834,707 A | 5/1989 | Evans |
| 4,840,626 A | 6/1989 | Linsky et al. |
| 4,878,890 A | 11/1989 | Bilweis |
| 4,936,857 A | 6/1990 | Kulik |
| 4,957,477 A | 9/1990 | Lundback |
| 4,960,424 A | 10/1990 | Grooters |
| 4,973,300 A | 11/1990 | Wright |
| 4,976,730 A | 12/1990 | Kwan-Gett |
| 5,057,117 A | 10/1991 | Atweh |
| 5,087,243 A | 2/1992 | Avitall |
| 5,098,369 A | 3/1992 | Heilman et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,336,254 A | 8/1994 | Brennen et al. |
| 5,352,184 A | 10/1994 | Goldber et al. |
| 5,356,432 A | 10/1994 | Rutkow et al. |
| 5,383,840 A | 1/1995 | Heilman et al. |
| 5,385,156 A | 1/1995 | Oliva |
| 5,385,528 A | 1/1995 | Wilk |
| 5,429,584 A | 7/1995 | Chiu |
| 5,433,727 A | 7/1995 | Sideris |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup III |
| 5,593,441 A | 1/1997 | Lichtenstein et al. |
| 5,603,337 A | 2/1997 | Jarvik |
| 5,647,372 A | 7/1997 | Tovey et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,749,839 A | 5/1998 | Kovacs |
| 5,782,746 A | 7/1998 | Wright |
| 5,800,528 A | 9/1998 | Lederman et al. |
| 5,848,962 A | 12/1998 | Feindt et al. |
| 5,849,005 A | 12/1998 | Garrison et al. |
| 5,853,422 A | 12/1998 | Huebsch et al. |
| 5,865,791 A | 2/1999 | Whayne et al. |
| 5,910,124 A | 6/1999 | Rubin |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A * | 6/2000 | Mortier et al. ............... 128/898 |
| 6,077,218 A | 6/2000 | Alferness |
| 6,085,754 A | 7/2000 | Alferness et al. |
| 6,095,968 A | 8/2000 | Snyders |
| 6,110,100 A | 8/2000 | Talpade |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 * | 2/2001 | Mortier et al. ............... 600/16 |
| 6,190,408 B1 | 2/2001 | Melvin |
| 6,193,648 B1 | 2/2001 | Krueger |
| 6,214,047 B1 | 4/2001 | Melvin |
| 6,221,103 B1 | 4/2001 | Melvin |
| 6,224,540 B1 | 5/2001 | Lederman et al. |
| 6,230,714 B1 | 5/2001 | Alferness et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,293,906 B1 | 9/2001 | Vanden Hoek et al. |
| 6,360,749 B1 * | 3/2002 | Jayaraman ............... 128/898 |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 * | 8/2002 | Wardle ............... 600/16 |
| 2002/0007216 A1 | 1/2002 | Melvin |
| 2002/0022880 A1 | 2/2002 | Melvin |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |

FOREIGN PATENT DOCUMENTS

| | | |
|---|---|---|
| FR | 2 645 739 A1 | 10/1990 |
| GB | 2 115 287 | 9/1983 |
| GB | 2 209 678 A | 5/1989 |
| JP | 60-203250 A2 | 10/1985 |
| JP | 1-145066 | 6/1989 |
| JP | 1/271829 | 10/1989 |
| SU | 1009457 A | 4/1983 |
| SU | 1734767 A1 | 5/1992 |
| WO | 91/19465 | 12/1991 |
| WO | 95/06447 | 3/1995 |
| WO | 96/04852 | 2/1996 |
| WO | 96/40356 | 12/1996 |
| WO | WO 97/20505 | 6/1997 |
| WO | 97/24101 | 7/1997 |
| WO | WO 98/14136 | 4/1998 |
| WO | 98/26738 | 6/1998 |
| WO | WO 98/29041 | 7/1998 |
| WO | WO 98/03213 | 1/1999 |
| WO | WO 99/30647 | 6/1999 |
| WO | 99/44534 | 9/1999 |
| WO | WO 99/44680 | 9/1999 |

| | | |
|---|---|---|
| WO | WO 99/53977 | 10/1999 |
| WO | WO 99/56655 | 11/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | 00/13722 | 3/2000 |
| WO | WO 00/16700 | 3/2000 |
| WO | 00/18320 | 4/2000 |
| WO | WO 00/28912 | 5/2000 |
| WO | WO 00/28918 | 5/2000 |
| WO | 00/45735 | 8/2000 |
| WO | WO 00/62727 | 10/2000 |
| WO | WO 01/50981 A1 | 7/2001 |
| WO | WO 01/67985 A1 | 9/2001 |
| WO | WO 01/85061 A2 | 11/2001 |
| WO | WO 01/91667 A2 | 12/2001 |
| WO | WO 01/95831 A2 | 12/2001 |
| WO | WO 01/95832 | 12/2001 |

OTHER PUBLICATIONS

Howard R. Ievin, M.D., et al., *Reversal of Chronic Ventricular Dilation in Patients With End–Stage Cardiomyopathy by Prolonged Mechanical Unloading, Circulation*, vol. 91, No. 11, Jun. 1995.

David A. Kass, M.D., et al., *Reverse Remodeling From Cardiomyoplasty in Human Heart Failure, Circulation*, vol. 91, No. 9, May 1, 1995.

Vinay Badhwar, et al., *Power Generation From Four Skeletal Muscle Configuration, Design Implications for a Muscle Powered Cardiac Assist Device, ASAIO Journal*, 1997; 43: M651–657, Dec. 1997.

Ray, C.–J. Chiu, *Using Skeletal Muscle for Cardiac Assistance, Scientific American*, Nov./Dec. 1994.

Cardiac Binding in Experimental Heart Failure, Mikhail Vaynblat, MD, et al., 1997 *by the Society of Thoracic Surgeons*, pp. 81–85, Dec. 1997.

The Effects of Prosthetic Cardiac Binding and Adynamic Cardiomyoplasty in a Model of Dilated Cardiomypathy, Joong Hwan Oh, MD, et al., *the Journal of Thoracic Cardiovascular Surgery*, vol. 116, No. 1, pp. 148–153, Dec. 1998.

Passive Ventricular Constraint Amends the Course of Heart Failure: A Study in an Ovine Model of Dilated Cardiomyopathy, J.M. Power, et al., *Cardiovascular Research* 44 (1999) 549–555, Dec. 1999.

Girdling Effect on Nonstimulated Cardiomyoplasty on Left Ventricular Function, Eli R. Capouya, M.D., et al, 1993 *by the Society of Thoracic Surgeons*, pp. 867–871.

Passive Epicardial Containment Prevents Ventricular Remodeling in Heart Failure, Pervaiz A. Chaudry, M.D., et al, 2000 *by The Society of Thoracic Surgeons*, pp. 1275–1280.

Passive Ventricular Constraint For the Treatment of Congestive Heart Failure, Mehmet C. Oz, MD, 2001 by *the Society of Thoracic Surgeons*, pp. S185–187, Dec. 2001.

Ventricular Containment as an Adjunctive Procedure in Ischemic Cardiomyopathy: Early Results, Jai S. Raman, et al., Ann (*Thorac Surg 2000*;70:1124–6), Dec. 2000.

Cardiothoracic Surgery, *Surgical Forum*, pp. 146–148, Dec. 1996.

Chaudhry, et al., *Acute Ventricular Reduction with Acorn's Cardiac Support Device Prevents Progressive Left Ventricular Dysfunction and Remodeling in Dogs with Advanced Heart Failure*, Henry Ford Heart and Vascular Institute, Detroit MI.

Teekell–Taylor, et al, *Passive Ventricular Restraint with Nitinol Mesh Attenuates Remodeling Following Acute Myocardial Infarction*, American College of Cardiology.

Bencini et al., *The "Pneumomassage" of the Heart*, Surgery Mar. 1956, vol. 39, No. 3, 1956.

*Abstracts of the 38$^{th}$ Scientific Sessions*, Oct. 1965.

Lev, M.D., et al., *Single (Primitive) Ventricle, Circulation*, vol. 39, May, 1969, pp. 577–591.

D.F. Paling, F.T.I., Warp Knitting Technology, 1970.

Edie, M.D. et al., *Surgical repair of single Ventricule*, The journal of Thoracic and Cardiovascular Surgery, vol. 66, No. 3, Sep., 1973, pp 350–360, 1973.

McGoon, M.D., et al., *Correction of the univentricular heart having two artioventricular valves*, The Journal of Thoracic and Cardiovascular Surgery, vol. 74, No. 2 Aug., 1977, pp. 218–226, 1977.

Doty, M.D., *Separation of the univentricular heart*, The Journal of Thoracic and Cardiovascular Surgery, vol. 78, No. 3, Sep., 1979, pp. 423–430, 1979.

Feldt, M.D., *Current status of the separation procedure for univentricular heart*, The Journal of Thoracic and Cardiovascular Surgery, vol. 82, No. 1, Jul., 1981, pp. 93–97, 1981.

*Myocarrdial Substitution with Simulated Skeltal Muscle: First Successful Clinical Case*, The Lancer, Jun. 1, 1985.

Arnstadt, et al., *Direct mechanical ventricular actuation: A review*, Resuscitation, 21 (1991) 7–23, 1991.

Arnstadt, et al., *Pulsatile Reperfusion After Cardiac Arrest Improves Neurological Outcome*, 1991.

Shumacker, *Cardiac Aneurysms*, The Evolution of Cardiac Surgery, 1992, pp. 159–168, 1992.

Savage, M.D., *Repair of left ventricular aneurysm*, 1992.

Vaynblat et al., "Cardiac Binding in Experimental Heart Failure" *Supplement to Circulation*, American Heart Association, vol. 92, No. 8, Oct. 5, 1995.

Jay N. Cohn, M.D., *The Management of Chronic Heart Failure*, The New England Journal of Medicine, vol. 335 No. 7, pp. 490–498, Aug. 15, 1996.

Westaby with Bosher, *Landmarks in Cardiac Surgery*, 1997, pp. 198–1991997.

Cox, *Left ventricular Aneurysms: Pathophysiologic Observations and Standard Resection*, Seminars in Thoracic and Cardiovascular Surgery, vol. 9, No. 2, Apr., 1997, pp. 113–122, 1997.

Capomolla, et al., *Dobutamine and nitroprusside infustion in patients with severe congestive heart failure: Hemodynamic improvement by discourdant effects on mitral regulation, left atrial function*, and ventricular function, American Heart Journal, Dec. 1997.

C. Coletta, *Prognostic value of left ventricular volume response during dobutamine stress echocardiography*, European Heart Journal (1997) 18, 1599–1605, 1997.

Francisco Torrent Guasp, *Una protesis contentiva para el tratamiento de la microcardiopatia dilatada*, Revista Espanola de Cardiologia, vol. 51, No. 7, Jul. 1998.

Melvin, *Ventricular Radius Reduction Without Restriction: A Computational Analysis*, ASAIO Journal, 45:160–165, 1999.

*Abstracts–Heart Failure*, JACC Feb. 1999.

Acorn Cardiovascular, Inc., *CSD Specifications Acorn Cardiac Support Device*, 2000.

McCarthy et al., *Device Based Left Ventricular Shape Change Immediately Reduces Left Ventricular Volume and Increases Ejection Fraction in a Pacing Induced Cardiomyopathy Model in Dogs: A Pilot Study*.

*Heart "jacket" could help stop heart failure progression*, Clinica 916, Jul. 2000, 2000.

Acorn Cardiovascular, Inc., *CorCap Cardiac Support Device, Patient Information Pamphlet*, Acorn Cardiovascular, Inc 6/2001.

*Medtronic's InSync Cardiac Resynchronization Therapy Device Approved By FDA*, 2001.

Acorn Cardiovascular, Inc., *Acorn Highlights: Esc*, Acorn Cardiovascular, Inc., Abstract Supplement, *European Heart Journal*, vol. 22, Sep. 2001.

* cited by examiner

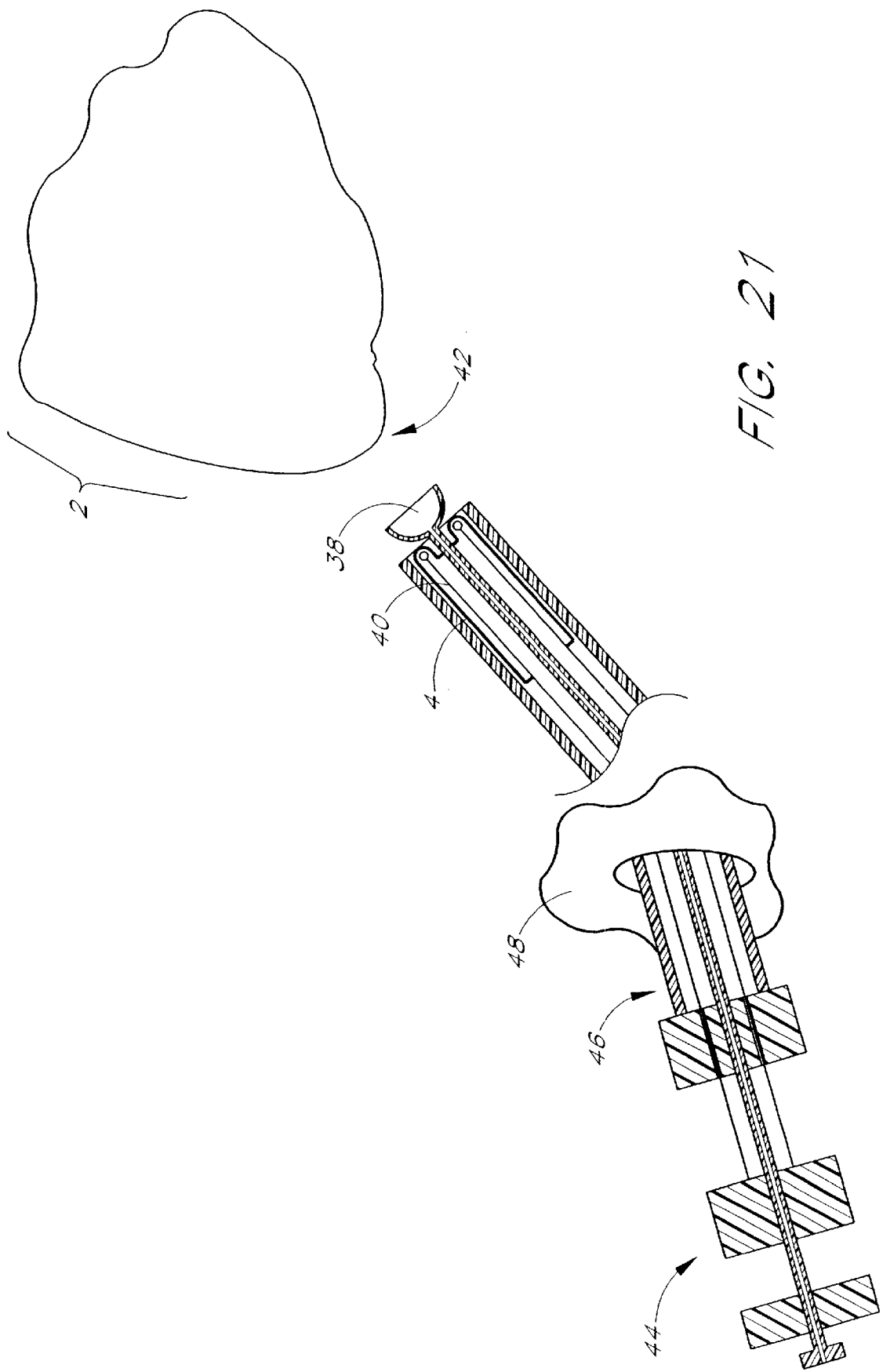

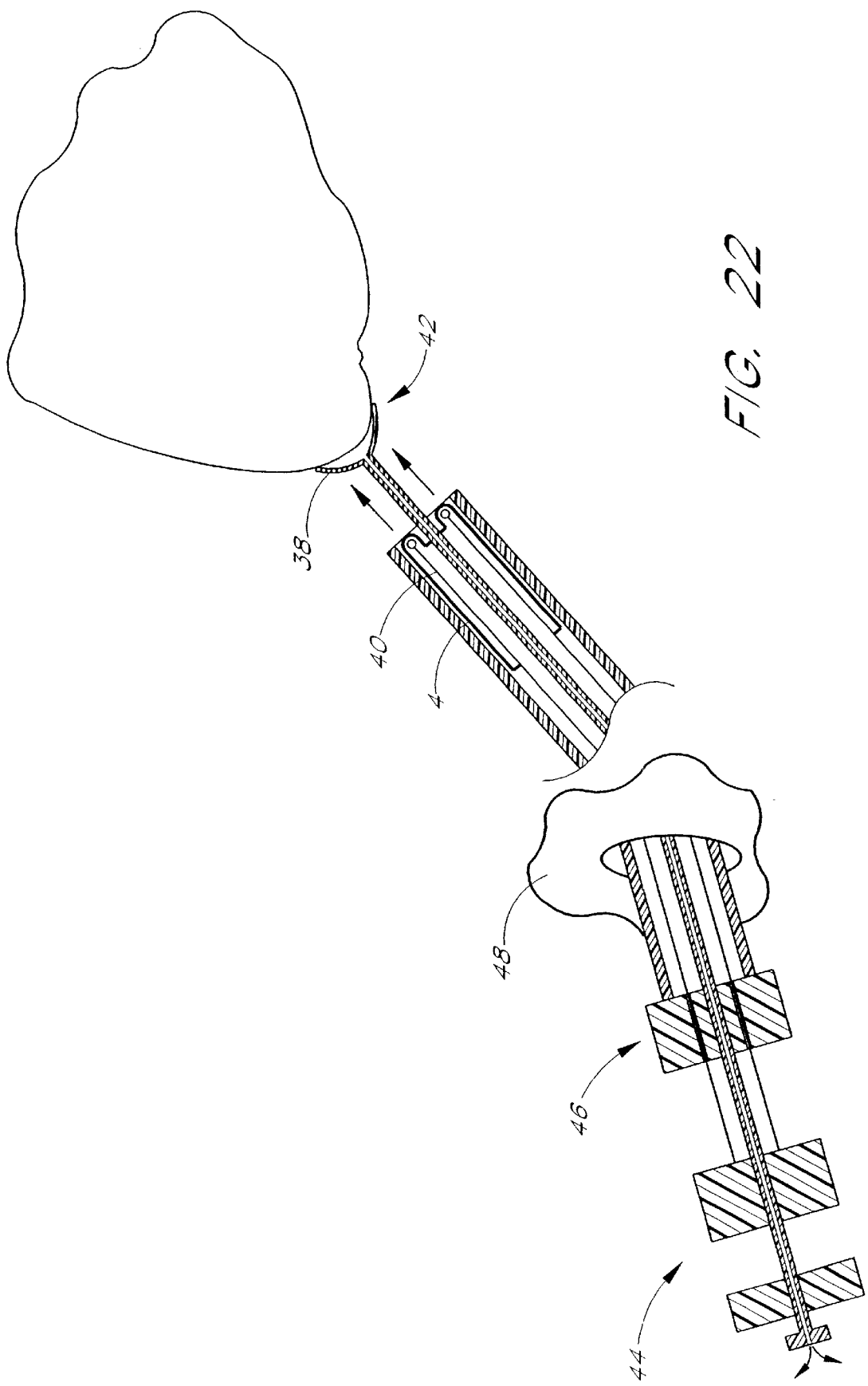

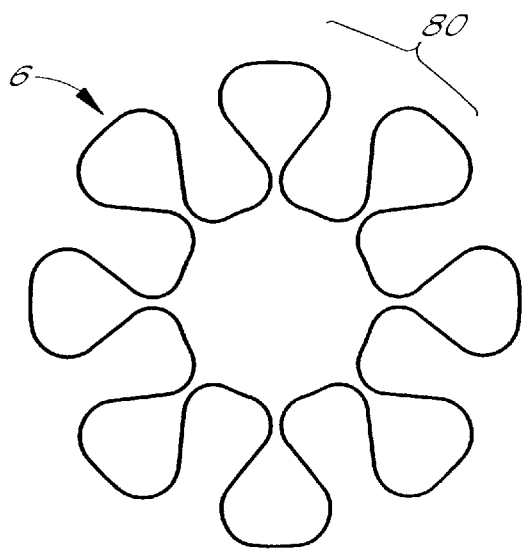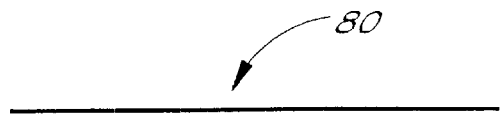
FIG. 35B
FIG. 35A
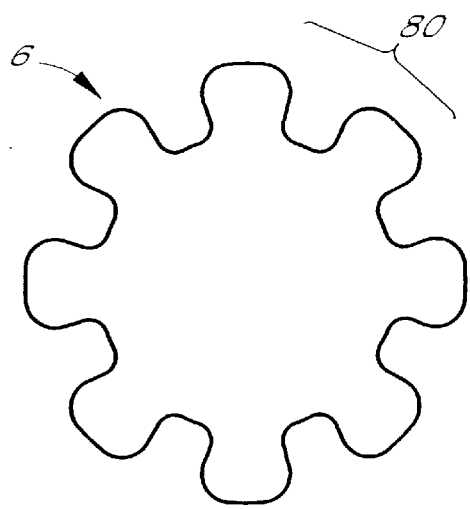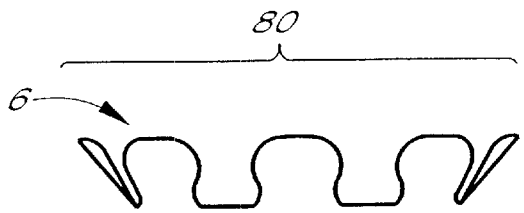
FIG. 36B
FIG. 36A

EXPANDABLE CARDIAC HARNESS FOR TREATING CONGESTIVE HEART FAILURE

RELATED APPLICATIONS

This application is a continuation of copending U.S. application Ser. No. 09/634,043, pending which was filed on Aug. 8, 2000, and which claims priority to U.S. application Ser. No. 60/188,282, which was filed on Mar. 10, 2000, and U.S. application Ser. No. 60/171,792, which was filed on Dec. 22, 1999.

BACKGROUND OF THE INVENTION

1. Field of the Invention

The present invention relates to mechanical systems for treating congestive heart failure. Specifically, the invention relates to devices that interface mechanically with a patient's failing heart in order to improve its pumping function.

2. Description of the Related Art

Congestive heart failure ("CHF") is characterized by the failure of the heart to pump blood at sufficient flow rates to meet the metabolic demand of tissues, especially the demand for oxygen. Historically, congestive heart failure has been managed with a variety of drugs. There is also a considerable history of the use of devices to improve cardiac output. For example, physicians have employed many designs for powered left-ventricular assist pumps. Multi-chamber pacing has been employed to optimally synchronize the beating of the heart chambers to improve cardiac output. Various skeletal muscles have been investigated as potential autologous power sources for ventricular assist. Among these, dynamic cardiomyoplasty using the latissimus dorsi muscle has attracted the most interest. It has been suggested that the beneficial effects of this procedure stem from both an active, dynamic, systolic assistance and a passive, adynamic girdling of the heart that limits diastolic stretch of the ventricle.

To exploit these beneficial clinical features, researchers and cardiac surgeons have experimented with prosthetic "girdles" around the heart. One such design reported in the literature is a prosthetic "sock" that is wrapped around the heart. Others have proposed the application of an intraventricular splint to reduce the volume of the left ventricle. Several design shortcomings are apparent with each.

The intraventricular splint, for example, extends through the left ventricular wall. Consequently, some components of the splint contact the patient's blood. This creates the potential for thrombogenesis, or the generation of blood clots. In addition, splint placement requires perforation of the ventricular wall, which may lead to leakage problems such as hemorrhage or hematoma formation. Furthermore, because one end of the splint extends to the epicardial surface of the left ventricle, options for the orientation of the splint are limited.

Pulling opposite walls of the ventricle closer together may reduce average wall stress via LaPlace's law, by reduction in ventricular diameter. However, this may create an irregular ventricular wall contour. This creates stress concentrations in the regions of the ventricle that are between the localized compression points. Consequently, this may lead to aneurysm formation, fibrosis, and impairment of the contractility and compliance of the ventricle. Also, the resulting irregular contour of the endocardial surface of the left ventricle may lead to localized hemostasis or turbulence, which may in turn lead to thrombus formation and possible thromboembolism.

Coronary artery disease causes approximately 70% of congestive heart failure. Acute myocardial infarction ("AMI") due to obstruction of a coronary artery is a common initiating event that can lead ultimately to heart failure. This process by which this occurs is referred to as remodeling and is described in the text Heart Disease, 5th ed., E. Braunwald, Ch. 37 (1997). Remodeling after a myocardial infarction involves two distinct types of physical changes to the size, shape and thickness of the left ventricle. The first, known as infarct expansion, involves a localized thinning and stretching of the myocardium in the infarct zone. This myocardium can go through progressive phases of functional impairment, depending on the severity of the infarction. These phases reflect the underlying myocardial wall motion abnormality and include an initial dyssynchrony, followed by hypokinesis, akinesis, and finally, in cases that result in left ventricular aneurysm, dyskinesis. This dyskinesis has been described as "paradoxical" motion because the infarct zone bulges outward during systole while the rest of the left ventricle contracts inward. Consequently, end-systolic volume in dyskinetic hearts increases relative to nondyskinetic hearts.

The second physical characteristic of a remodeling left ventricle is the attempted compensation of noninfarcted region of myocardium for the infarcted region by becoming hyperkinetic and expanding acutely, causing the left ventricle to assume a more spherical shape. This helps to preserve stroke volume after an infarction. These changes increase wall stress in the myocardium of the left ventricle. It is thought that wall tension is one of the most important parameters that stimulate left ventricular remodeling (Pfeffer et al. 1990). In response to increased wall tension or stress, further ventricular dilatation ensues. Thus, a vicious cycle can result, in which dilatation leads to further dilatation and greater functional impairment. On a cellular level, unfavorable adaptations occur as well. This further compounds the functional deterioration.

Some have proposed that an elastic wrap around the heart might attenuate the remodeling process that is actively underway in failing hearts, prompting treatment with latissimus dorsi cardiomyoplasty. Based on experimental work to date, passive latissimus dorsi muscles appear to be best suited for this application. Oh et al. (1997) published experimental work in which they found a relatively inelastic prosthetic fabric wrap to be inferior to adynamic latissimus dorsi in bringing about reverse remodeling in an experimental model of heart failure. This was attributed to the greater elasticity of the muscle wrap.

It is thought that application of a device to provide compressive reinforcement similar to that of adynamic cardiomyoplasty might be therapeutic in treating dilated, failing hearts. Because heart failure is only the clinical end-stage of a continuous remodeling process, such a device might be able to attenuate or stop remodeling after a myocardial infarction far before the onset of heart failure. Such a device would have different functional requirements from a device that is used solely to treat established heart failure.

One requirement is to provide a slight elastic compression to the epicardial surface of the left ventricular wall. The device should allow expansion and contraction of the heart, but continue to apply gentle elastic compression to the left ventricle. This would reduce circumferential and longitudinal wall tension, thereby improving efficiency, lowering energy expenditure, reducing neurohormonal activation, encouraging favorable cellular changes, and stabilizing the dimensions of the heart. This mechanical action is often referred to as "myocardial sparing." The device should effect myocardial sparing without limiting the motion or the dimensions of the heart. Nor should it actively change the shape of the heart by pulling it or squeezing it. In fact, imposing a rigid barrier to limit distension or to squeeze the heart can be potentially dangerous. Shabetai in The Role of the Pericardium in the Pathophysiology of Heart Failure notes that the pericardium exerts 3–4 mm Hg of pressure against the heart. Cardiac function can be adversely affected with just a slight increase in pericardial constraint. For example, cardiac tamponade begins to be seen with pericardial pressures as low as 5–10 mm Hg.

A second requirement of such a device is to provide reinforcement that prevents the further shape change of the left ventricle without acutely changing the shape by its application. The device would act to prevent both global dilatation toward a more spherical shape and local infarct expansion after a myocardial infarction. In fact, if the local infarct expansion can be minimized with such a device, the compensatory global dilatation and increase in sphericity may be prevented. What is needed is a mild compressive support that conforms to the epicardial contour. As the left ventricle or portions of the left ventricle distend outward, they would be met with greater pressure from the device. The presence of the device would likely cause the left ventricle to reverse-remodel and its dimensions to stabilize and even shrink. As this occurs, the device would be able to shrink with the left ventricle like a latissimus dorsi muscle. The device would supply less pressure as the diameter decreases. Conversely, the device would supply gradually increasing pressure as the diameter or local distention increases. This ideal was expressed by Oh et al. in their description of the benefits of a passive latissimus dorsi muscle wrap.

The ability of the device to conform to the heart as it shrinks or expands is of great importance. A device would need to possess considerable elasticity in order to do so. The left ventricle in a dilated, failing heart does not distend significantly because small diameter changes are sufficient to achieve the necessary stroke volume. In contrast, a normal heart has a much smaller left ventricular diameter. For example, Li (1997) noted that to achieve a 70-cc stroke volume, a normal left ventricle of 2.8 cm radius contracts down to 1.7 cm, a 40% decrease. However, a dilated ventricle of 4.5-cm radius achieves the same stroke volume by contracting to 4.2 cm, only a 7% decrease. Thus, in order to achieve the same stroke volume as a dilated heart, the normal heart's ventricular diameter must change by a greater amount. Consequently, a device with sufficient elasticity for treating dilated hearts in established heart failure may not be able to treat a heart of normal dimensions that has suffered a myocardial infarction.

The ability of a harness to conform to the heart is also theoretically important in preventing dilated heart failure after acute myocardial infarctions because it may be important to provide reinforcement during systole, especially early systole. Prosthetic fabrics impose a relatively inelastic barrier that acts only at the end-limits of diastole. In addition to providing more myocardial sparing over a greater portion of the cardiac cycle, a device that remains in compressive contact with the heart into systole would counteract the "paradoxical bulging" of the infarct region that occurs in dyskinetic, aneurysmal hearts during systole. This may attenuate infarct expansion and therefore limit the extent of remodeling that further ensues.

Another problem with the inelastic nature of fabric wraps, or knits, is that normal, healthy changes in the dimensions of the heart are not accommodated. In addition to chronic pathologic changes in ventricular diameter that can occur, such as those that accompany remodeling, normal physiological changes also occur. For example, in order to keep up with increased metabolic demands from physical exertion or exercise, the heart may dilate acutely. A wrap must be able to accommodate these increases without imposing excessive pressures.

An important problem with the use of fabrics, such as knits and weaves, as well as with other materials previously used for this application, is their dimensional coupling between orthogonal directions. When stretched in one direction, there is considerable foreshortening in the perpendicular direction. Typically, the greater the elasticity present, the greater the foreshortening that is seen in the perpendicular direction. When used in a wrap around the heart, such a material can lead to serious problems. The greatest distension and wall stress is oriented in the circumferential direction around the left ventricle. Therefore it is logical to align the more compliant direction of the fabric to be parallel to it. As the left ventricle fills and the diameter increases, the fabric stretches in the circumferential direction. This causes shortening in the longitudinal direction, which is perpendicular to the direction of stretch. When used in a cardiac wrap, this results in increased sphericity of the ventricle during diastole, relative to the unwrapped heart. Sphericity is defined as the ratio of the diameter to the length of the heart or ventricle. Increased sphericity of the left ventricle is associated with decreased survival and an increased incidence of mitral regurgitation. Kono (1992) and Douglas (1989) documented this in published studies. There is a need for a structure that does not foreshorten and increase sphericity as it provides elastic, compressive reinforcement to the heart, especially the left ventricle.

Since the mid 1980's a promising procedure has been evaluated clinically. The procedure, dynamic cardiomyoplasty, involves surgically dissecting the patient's latissimus dorsi muscle, introducing it into the thoracic cavity, and then wrapping and attaching the muscle to the heart. An implantable electrical stimulator is connected to the muscle in order to stimulate and pace it in synchrony with the heart. This causes the muscle to contract and also transforms the muscle, making it more fatigue-resistant. The original premise behind dynamic cardiomyoplasty was that these muscle contractions, by virtue of the geometry of the wrap, would squeeze the heart, and thus provide systolic assistance. If successful, an essentially patient-powered, relatively inexpensive, non-blood-contacting, easily placed ventricular-assist device could be employed.

The first reported clinical case of dynamic cardiomyoplasty using a latissimus dorsi wrap was published in 1985. Since then, over 1,000 patients have been treated with this experimental procedure. Numerous published studies have shown that the procedure produces significant improvement in clinical status, as graded by the New York Heart Association ("NYHA") classification scale, a slight but significant hemodynamic or systolic function improvement, and a reduction in the number of patient hospital visits after the procedure. However, an improvement in survival has yet to be consistently demonstrated. Furthermore, perhaps due to their frail condition, NYHA class IV patients have not fared well with the procedure. This has limited its use to NYHA class III patients. It appears that the skeletal muscle wrap, probably because of its deterioration over time, does not provide sustained squeezing of the heart over time. Yet, the clinical benefits of the procedure appear to persist. This paradox has led to considerable research into the underlying mechanisms of dynamic latissimus dorsi cardiomyoplasty.

This research has resulted in several independently additive hypothetical mechanisms to explain the benefits of dynamic cardiomyoplasty. The original concept of systolic squeezing of the heart, in particular the left ventricle, was shown in experimental work to provide hemodynamic benefit. But there additionally appears to be a considerable benefit derived from the presence of the passive, unstimulated latissimus dorsi wrap alone. Drs. Chiu (1992), Carpentier (1993), and others hypothesized that the presence of the latissimus dorsi wrap provides a beneficial passive function beyond, the benefits of systolic-squeezing augmentation. It was speculated that the muscle wrap acts as a girdle around the heart. The girdle is thought to impose a physical limit on the heart to prevent it from dilating beyond its boundaries. This is commonly referred to as the "girdling" effect. A separate and equally powerful hypothesis was that the muscle wrap helps the native myocardium bear some of the load, in essence reducing myocardial tension or wall stress, via Laplace's law, by creating a thicker wall. This has been referred to as the "myocardial sparing" effect by virtue of the reduction in wall stress and concomitant reduction in oxygen consumption. The benefits of these two passive mechanisms are thought to be additive with the systolic squeezing benefits of cardiomyoplasty. Published experimental work by Nakajima et al. (1994), Chen et al. (1995), Kawaguchi et al. (1992 & 1994), Kass et al. (1995), Capouya et al. (1993), Chekanov (1994) and others provide support to the validity of the hypothetical mechanisms.

The concept of using a permanently implantable passive, non-contracting wrap around the heart to prevent its further deterioration is not new. Suggestions have been published in the literature. Kass et al. (1995) questioned whether an "artificial elastic sock" could be used in lieu of skeletal muscle. They speculated that in dynamic cardiomyoplasty, the latissimus dorsi wrap provides some of its benefit by acting as an elastic constraint around the epicardial surface. They further suggest that the passive skeletal muscle wrap stiffens gradually with stretch, unlike pericardium, which is highly compliant at low levels of stretch but becomes very stiff when expanded beyond resting dimensions. Throughout the article, the importance of gradually increasing stiffness over the entire range of cardiac operating dimensions is emphasized. Despite the conceptual discussion; however, there is no mention of how a cardiac wrap that is both elastic over the entire range of cardiac dimensions and gradually stiffens with stretch can be designed or built.

Vaynblat et al. (1997) report on the experimental use of an expanded polytetrafluoroethylene ("ePTFE") prosthetic wrap in animals. They constructed the wrap from sheets of ePTFE material that were sized to the heart and sutured to finish the wrap. ePTFE has very limited elasticity and stretch. The ePTFE sheet wraps were shown to reduce ventricular dilatation in a failing-heart model, but they did not improve cardiac function.

Oh et al. (1998) report on a similar study using a Marlex polypropylene mesh sheet material. In this study they compared the benefits of unpaced, adynamic latissimus dorsi muscle wraps with those constructed of Marlex sheet material. It was found that the latissimus dorsi wrap attenuated dilatation of left ventricle in a failing heart model to a greater extent than the Marlex wrap. The superiority of the latissimus dorsi wrap was attributed largely to its "elastic stretchability" and the resulting dynamic constraint that it provided. This "yield-and-support" characteristic could not be attained using prosthetic membranes, such as Marlex and ePTFE. In addition, the fibrotic reactions that are likely to be induced by the prosthetic membranes have a further adverse effect on compliance. In further support of the contention made by Kass, Oh et al. state that pericardium "shows virtually no restraining effect on chronic cardiac dilatation." Despite this, the authors mention that latissimus dorsi cardiomyoplasty, whether dynamic or adynamic, is a very invasive and complex surgical procedure. The exclusion of NYHA Class IV patients from the dynamic cardiomyoplasty clinical trials was partially attributed to this. Oh et al. suggest that cardiac binding with a prosthetic membrane may still be of value, even with shortcomings, because it lends itself to minimally invasive surgical techniques.

None of these prosthetic cardiac wraps operates elastically in this manner over the entire range of cardiac dimensions. Thus, only an "end-girdling" effect is provided. The myocardial sparing effect is only present for a brief moment at the end of diastole. In addition, because these inelastic wraps counteract dilatation at the limits of diastole, they prevent the heart from expanding beyond that dimensional limit to accommodate increased physiological demand, such as during exercise. In addition, even if the wraps could bring about desirable reverse-remodeling and shrinkage of the heart, a wrap, due to its fixed circumference, may not be able to shrink evenly with a heart whose circumference is decreasing. In fact, the prosthetic wraps may interact with the heart like a fiber-reinforced composite material and even fix or "cement" the circumference and diameter of the heart, such that it is unable to shrink.

Because the three underlying mechanical mechanisms of dynamic cardiomyoplasty discussed above are considered to be independently additive, it is thought that the addition of active systolic assistance to the heart would be more beneficial than a passive wrap alone. In a published experiment by Mott et al. (1998), dynamically paced latissimus dorsi was compared with unpaced, adynamic latissimus dorsi in an experimental heart failure model. It was found that the dynamic, paced wrap was capable of reversing remodeling to a much greater extent than an unpaced latissimus dorsi wrap. Mott et al. also speculate that perhaps the dynamic and adynamic functions of latissimus dorsi wraps provide complimentary benefit to failing hearts. The adynamic wrap provides reinforcement only during diastole, while the dynamic wrap provides reinforcement during systole.

Additional support for this idea can be found in published anecdotal reports of documented hemodynamic deterioration in patients in whom cardiomyostimulators malfunctioned and ceased to provide stimulation to the latissimus dorsi wrap. This further suggests that the systolic assistance mechanism may provide increased benefit compared to a passive girdle alone.

Despite the prevailing sentiment that stimulated latissimus dorsi wraps should be more beneficial than non-stimulated wraps, the manner in which dynamic cardiomyoplasty has been executed clinically has limited its clinical success and therefore its acceptance. The underlying mechanisms of dynamic cardiomyoplasty have been the focus of substantial investigation.

Preservation of the latissimus dorsi as a power source has also been an issue. Because of muscle atrophy and fibrosis, the amount of squeezing power that is available has not been sustainable. Ischemia, especially to the distal portion of the muscle whose blood supply was interrupted by surgical dissection, has been considered to be a major cause. In addition, some have speculated that damage to the thoracodorsal nerve during the procedure and as a result of the relocation of the muscle is a cause of loss of contractility of the muscle. Another possible problem is the unnatural configuration in which the muscle is forced to operate. The preloads and afterloads against which the muscle works are clearly altered from those of in situ latissimus dorsi.

The complexity and invasiveness of the dynamic cardiomyoplasty surgical procedure has been implicated as well. Even if the muscle were to remain viable in the long term, there are some physical limitations to its ability to provide the systolic assistance that was once the hope of dynamic cardiomyoplasty. Cho et al. (1994) published a study in which three-dimensional magnetic resonance imaging (3-D MRI) reconstruction was used to analyze experimental dynamic cardiomyoplasty. The authors found that muscle wrap stimulation brought about considerable translation of the heart in the plane of the short axis of the left ventricle and rotation about the long axis. Little short-axis or radial squeeze was seen. However, long-axis compression was observed. This long-axis compression was confirmed in a similar study published by Pusca et al. (1998). This suggests that the muscle power provided by the latissimus dorsi is not channeled very efficiently into systolic assistance.

One observation by Hayward is especially noteworthy. The author suggested that the contractile properties of the distal portion of the latissimus dorsi muscle in dynamic cardiomyoplasty degenerates the most. This is attributed to ischemia and the use of the muscle in an inefficient configuration. Yet, this is the portion of the muscle that is in contact with and expected to squeeze the heart. The proximal portion of the muscle, which is better perfused and oriented in a more linear, efficient, and natural configuration, does not contact with the heart. As such, stimulation of the muscle is likely to result in more contraction of the proximal portion of the muscle, the portion that does not squeeze the heart. Contraction of this portion of the muscle causes the heart to translate and rotate as observed experimentally by Cho. Because the heart is attached to the great vessels at its superior end, it would be expected to behave as if it were attached to a pivot at this point. Thus, any lateral force or moment applied to the heart should result in lateral translation and rotation. However, in this superior-pivot hypothesis, there should be less freedom to translate vertically. Therefore, any vertical force applied to the heart would likely cause longitudinal compression rather than translation. Thus, it is not surprising that stimulation of the muscle results in more translation, rotation, and lifting of the entire heart.

Even if the distal portion of the latissimus dorsi muscle remains viable, there may be a physical limit to how much systolic hemodynamic benefit it can provide. The overall volume of the left ventricle is more sensitive to changes in its short-axis dimension, i.e., its diameter, than its long-axis dimension, i.e., its length. For example, the volume of a cylinder is proportional to its length and to the square of its diameter. It would thus be expected that the greatest change in volume could be brought about by a change in the diameter of the ventricle. Skeletal muscle such as the latissimus dorsi is capable of shortening less than 15% over its length. Assuming that the muscle is adhered to the epicardium, the circumference of the heart would only be capable of shortening 15%. For approximation purposes, the left ventricle can be treated as a cylinder. If the circumference of a cylinder of 5-cm diameter shortens by 15%, then the volume of the cylinder changes by approximately 28%. It is interesting to note that this number is consistent with the maximum ejection fractions that have been achieved clinically and experimentally. A device that does not have the limitation of 15% stretch or shortening might be able to overcome this ejection-fraction limitation and provide more hemodynamic improvement, particularly in cardiac output. Poor increases in ejection fraction and cardiac output have been cited as a shortcoming of the dynamic cardiomyoplasty procedure.

Another limitation of dynamic cardiomyoplasty is the potential mismatch between the orientation of the direction of shortening of the latissimus dorsi muscle fibers and that of the epicardium. The principal direction of shortening corresponds to the direction of muscle fiber orientation of each. Although the myocardial muscle fiber orientation varies in the left ventricle, the principal direction of shortening has been reported to follow the epicardial muscle fiber orientation, which follows a left-handed helical orientation from the apex to the base of the chamber. If it is assumed that the latissimus dorsi becomes adhered to the epicardial surface of the heart, then any misalignment between the muscle fibers would result in inefficiency of energy transfer. Each muscle shortens and stretches somewhat across the "grain" or fiber direction of the other. To compound matters, Strumpf et al. (1993) report a significant increase in the stiffness of passive skeletal muscle in the cross-fiber direction. As a result, the muscle wrap may limit the extent of myocardial lengthening and shortening, and thus limit cardiac function.

An additional source of drag may stem from the inertia added by the muscle itself. It is estimated that an adult latissimus dorsi muscle weighs roughly 600 grams. This additional weight adds considerable inertia to the heart. This may be responsible for the reported impairment of cardiac function immediately following the application of the muscle by Corin et al. (1992), Cheng et al. (1992), and as suggested by Vaynblat et al. (1997).

Experimentally, passive, unstimulated latissimus dorsi cardiomyoplasty wraps appeared to be the best at attenuating remodeling and heart failure. However, in a clinical setting, the surgery required to dissect and attach the muscle around the heart is very extensive and traumatic. Even if such a therapy were proven clinically efficacious, this factor limits its potential acceptance.

Accordingly, there is still a need in the art for a prosthetic elastic wrap that does not foreshorten in the direction perpendicular to the primary direction of ventricular expansion, and that reduces wall stress by maintaining compressive contact over a significant portion of the cardiac cycle. Additionally, there is a need for a device that aids in preventing, in addition to treating, heart failure after acute myocardial infarction through attenuation of the remodeling process.

SUMMARY OF THE INVENTION

Accordingly, it is a principal object and advantage of the present invention to overcome some or all of the aforementioned disadvantages. One aspect of the present invention comprises a cardiac harness for treating or preventing congestive heart failure. The harness comprises a plurality of interconnected elastic bending hinges, each of which has a central portion connected on opposite sides to respective arm portions. The arm portions interact with the central portion in response to deflection of the arm portions to create a bending moment in the hinge to store potential energy.

In certain embodiments, the cardiac harness comprises bending hinges that are substantially U-shaped, V-shaped, square-wave-shaped, teardrop-shaped, or keyhole-shaped. Advantageously, at least one of the bending hinges from a first row is connected to another of the bending hinges from a second row.

In some preferred embodiments, the bending hinges comprise at least one strand of Nitinol. The strand(s) can comprise a wire or a ribbon.

In some embodiments, the cardiac harness further comprises a power source that supplies energy to the harness, causing the harness to contract. That power source may deliver electrical energy to at least one of the bending hinges, causing at least one of the bending hinges to produce a bending moment. Alternatively, the power source may deliver mechanical energy to the cardiac harness, such as through a cable. Advantageously, the power source is programmable via transcutaneous radiofrequency signals, and can be rechargeable via transcutaneous electromagnetic coupling, and/or transcutaneous inductive field coupling.

In another aspect of the invention, the cardiac harness has a plurality of spring elements, and the harness is adapted to be placed around at least a cardiac base. The spring elements interact such that the harness expands and contracts in a substantially transverse dimension of the harness in the region of the cardiac base in response to the mechanical cardiac cycle, without substantial expansion or contraction in the longitudinal dimension of the harness in the region of the cardiac base.

In another aspect of the invention, the cardiac harness is adapted to be placed around at least a cardiac apex. The spring elements interact such that the harness expands and contracts in a substantially longitudinal dimension of the harness in the region of the cardiac apex in response to the mechanical cardiac cycle, without substantial expansion or contraction in the transverse dimension of the harness in the region of the cardiac apex.

Another aspect of the invention includes at least one elongate strip sized to fit around a base of a ventricle, such that the strip extends substantially transverse to the longitudinal axis of the heart. The strip comprises at least one spring element configured to cause the strip to provide force against the base of the ventricle in a substantially transverse direction without substantial force in a longitudinal direction. The strip can comprise at least one undulating strand.

In some embodiments, the spring element comprises a central portion and two arm portions.

In another aspect, the harness of the disclosed embodiments can treat or prevent congestive heart failure in a heart having a ventricle that changes sphericity in response to diastolic filling. The harness comprises a plurality of interconnected spring elements, limiting diastolic distention of the ventricle to a degree of expansion without substantially altering naturally occurring changes in the sphericity of the ventricle through the same degree of expansion caused by diastolic filling of the, heart. Alternatively, the harness can limit diastolic distention of the ventricle to a degree of expansion while substantially decreasing the magnitude of a naturally occurring increase in the sphericity of the ventricle through the same degree of expansion caused by diastolic filling.

In another aspect of the invention, the harness comprises a series of interconnected spring elements, each spring element comprising a central portion and a pair of arm portions extending along respective paths that originate at respective sides of the central portion and converge toward each other along at least a portion of the paths as the paths extend away from the central portion.

In a further aspect, the harness comprises first and second strands of material, each strand having a plurality of hinges. Each of the hinges is formed by a pair of arm portions extending from a central portion, and each hinge within the plurality of hinges of the first strand has both arm portions disposed within a hinge of the second strand, between the arm portions of the hinge of the second strand. In some embodiments, at least one of the strands comprises a band.

Also disclosed is a method of assembling a cardiac harness, comprising providing a plurality of rings, each of the rings having a series of periodic undulations, each of the rings being unattached to other of the rings, and interconnecting the rings by interleaving the undulations without interrupting continuity of the rings.

In certain embodiments, the cardiac harness comprises interconnected strands of material. The harness also has at least one pad having a marginal edge which is oriented for placement in proximity to at least one coronary artery, so as to reduce compression of the artery by the harness. In further embodiments, the harness comprises interconnected strands of material which traverse an exterior surface of a ventricle of the heart, without traversing a substantial portion of the length of at least one of the following coronary arteries: the left anterior descending artery, the right coronary artery, the left circumflex artery, the posterior descending artery, and the obtuse marginal artery. And in some embodiments, the harness comprises a support member which supports a portion of the strands, the member having side portions disposed on opposite sides of the at least one coronary artery.

Also disclosed is an apparatus for delivering a cardiac harness having side portions and an apex portion. The apparatus comprises a catheter body having a distal end portion, configured to retain the harness in a substantially inverted condition with an interior side of the harness facing outward away from a ventricle and an exterior side facing inward toward the ventricle. The apparatus further comprises an activation member which is movable distally relative to the catheter body. The apex portion of the harness is releasably connected to the catheter body. The activation member drives the side portions of the harness distally and outwardly relative to the apex portion such that the harness expands circumferentially. The harness thereby everts to at least partially surround the ventricle, with the interior side of the harness facing inward toward the ventricle and the exterior side facing away from the ventricle. In some embodiments, the distal end portion comprises a suction cup.

Another aspect of the invention includes a method of delivering a cardiac harness onto a heart. The method comprises providing a catheter having an inverted harness mounted on a distal end portion of the catheter, inserting the catheter into a thorax such that an apex portion of the inverted harness is proximate to the apex of a ventricle, and everting side portions of the harness while the apex portion of the harness remains positioned proximate to an apex of the ventricle.

Also disclosed is a method of manufacturing a cardiac harness. The method comprises forming an elongate member having undulations from a sheet of material. In a preferred arrangement, forming the elongate member comprises forming the undulations in a plane substantially parallel to the sheet of material. In some embodiments, forming the elongate member comprises cutting the elongate member on a flat surface, and in certain arrangements, the method further comprises annealing the material with the undulations oriented at a substantial angle relative to the plane.

Further features and advantages of the present invention will become apparent to one of skill in the art in view of the Detailed Description of the Preferred Embodiments which follows, when considered together with the attached drawings and claims.

BRIEF DESCRIPTION OF THE DRAWINGS

FIGS. 21–25 are schematic illustrations of progressive steps in the application of the cardiac harness to a heart, utilizing the cardiac harness delivery device.

FIG. 35a is a schematic top view of a ring of hinges after being cut from a sheet of material.

FIG. 35b is a schematic side view of a ring of hinges after being cut from a sheet of material.

FIG. 36a is a schematic top view of a ring of hinges after being twisted into a beveled configuration.

FIG. 36b is a schematic side view of a ring of hinges after being twisted into a beveled configuration.

DETAILED DESCRIPTION OF THE PREFERRED EMBODIMENTS

Figure 1:
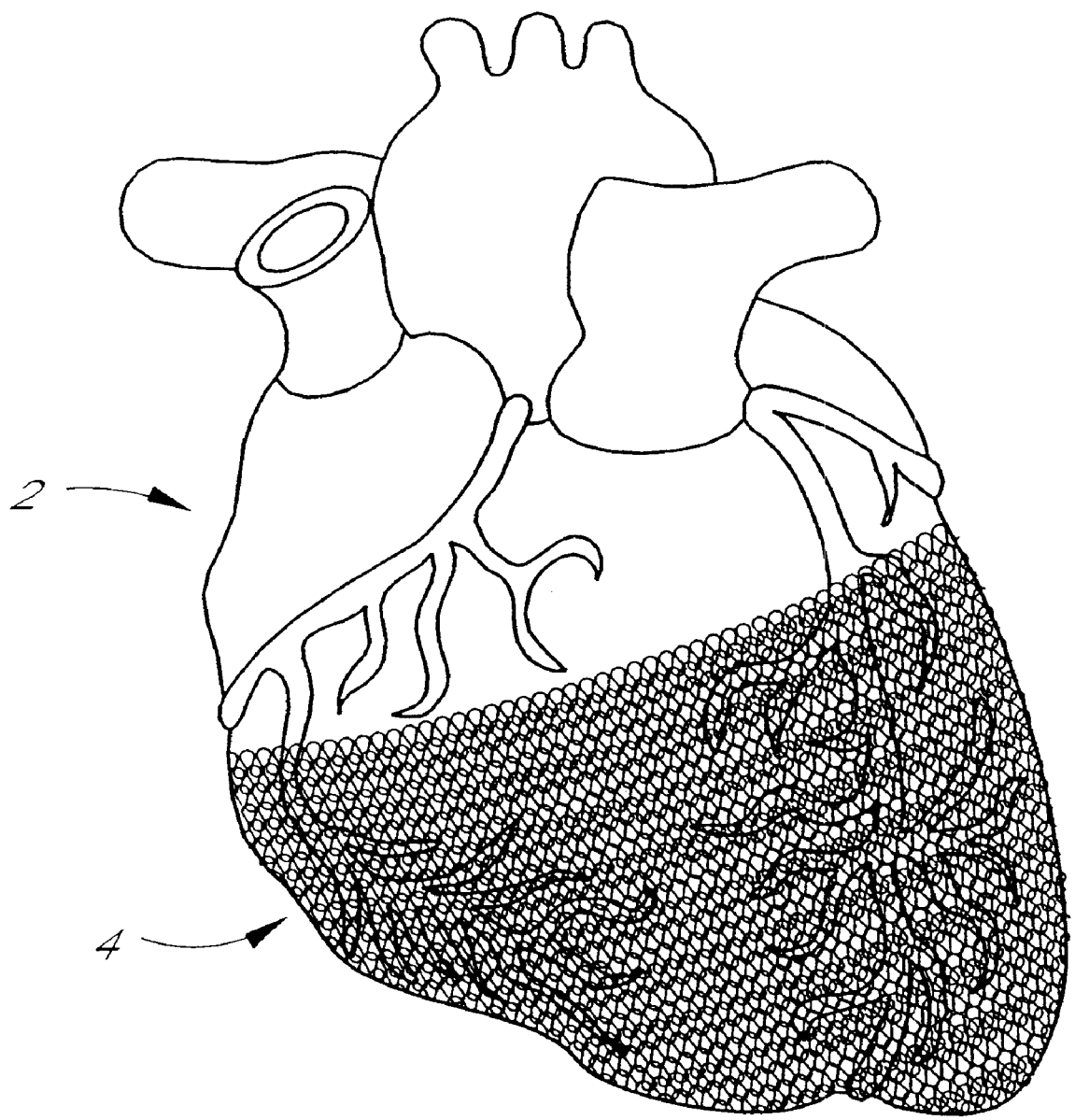
FIG. 1 is a schematic view of the mammalian heart, with the cardiac harness in place on the heart.

The preferred embodiment comprises an apparatus and method for treating established congestive heart failure ("CHF"), as well as for preventing its onset after acute myocardial infarction. Although reference is frequently made throughout this discussion to CHF caused by acute myocardial infarction, the cardiac harness of the disclosed embodiments can be used to treat CHF caused by forward-pump failure from any disease, such as idiopathic dilated cardiomyopathy, hypertrophic cardiomyopathy, and viral cardiomyopathy. The harness acts by the application of a elastic compressive reinforcement on the left ventricle to reduce deleterious and excessive wall tension and to resist shape change of the left ventricle during diastole. Use of this harness can attenuate and potentially reverse the remodeling process that occurs in the left and/or right ventricle following myocardial infarction.

The harness applies compressive reinforcement around the left ventricle over a significant portion of the cardiac cycle while minimizing change to the shape of a ventricle and heart. Rather than imposing a dimension beyond which the heart cannot expand, the preferred embodiment attempts to set no distinct limit to end-diastolic volume. Instead, the apparatus of the preferred embodiment follows the contour of the epicardium and continuously applies a gentle resistance to wall stretch. This avoids the potential to create dangerous restrictive and constrictive conditions, similar to those seen in restrictive cardiomyopathy, constrictive pericarditis, and cardiac tamponade.

A great advantage of the harness of the disclosed embodiments is its elasticity. Elasticity refers to the ability of a material or object to deform and recover its shape when a load is first applied and then removed from it. The greater the deformation from which it can recover, the greater is the elasticity of the material or object. Elasticity allows the cardiac harness to conform and apply pressure to the heart as it fills and empties. Elasticity of the harness is achieved by the use of hinges, which can be U-shaped, that bend elastically under load. These hinges can be arrayed or networked in various ways to impart a desired amount of support in a desired orientation, at a desired location. Another advantageous aspect of the cardiac harness is that the hinges are arranged so as to minimize or avoid foreshortening, especially in the longitudinal direction during circumferential expansion. This allows the device to reinforce the heart without necessarily altering the heart's sphericity to a great degree.

In addition to providing passive elastic support of the heart, the device can also provide an interface to the heart that allows the application of noncardiac power to assist systolic ventricular function.

A preferred embodiment comprises an array of connected hinge elements that are configured to be in compressive contact with the left ventricle. In another preferred arrangement, the connected hinge elements are in contact with the right ventricle or with both ventricles. The array of hinge elements provides selective elastic resistance to stretch during diastole and contractile augmentation during systole. Typically, elastic materials resist deformation with a force that increases with increasing deformation. This force is stored in the material and is released during the unloading of the material. Because wall stress in the left ventricle is thought to be greatest in the circumferential direction, the hinges are predominantly aligned to act in this direction, although it may be desirable to have some elastic support in the longitudinal direction, or some other direction, as well.

FIG. 1 illustrates a mammalian heart 2 with the cardiac harness 4 applied to it. In this illustration, the cardiac harness surrounds both ventricles, from apex to base. Note that the hinges are relatively small in this illustrated embodiment, but in other preferred embodiments, the hinges can be larger.

Figure 2A:
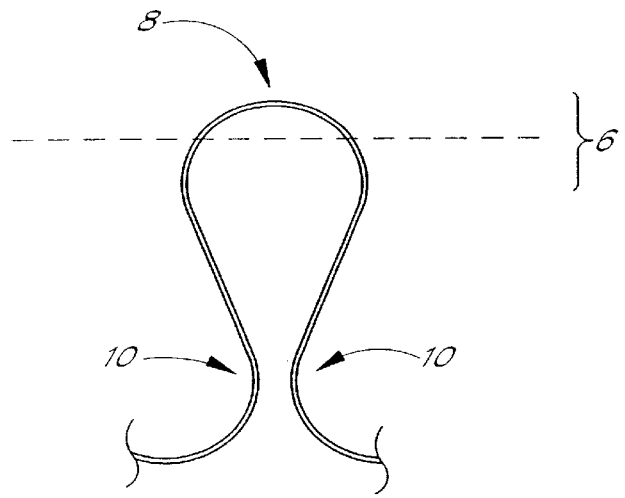
FIGS. 2A–2C illustrate an elastic bending hinge, both in a relaxed position and under tension.
Figure 2B:
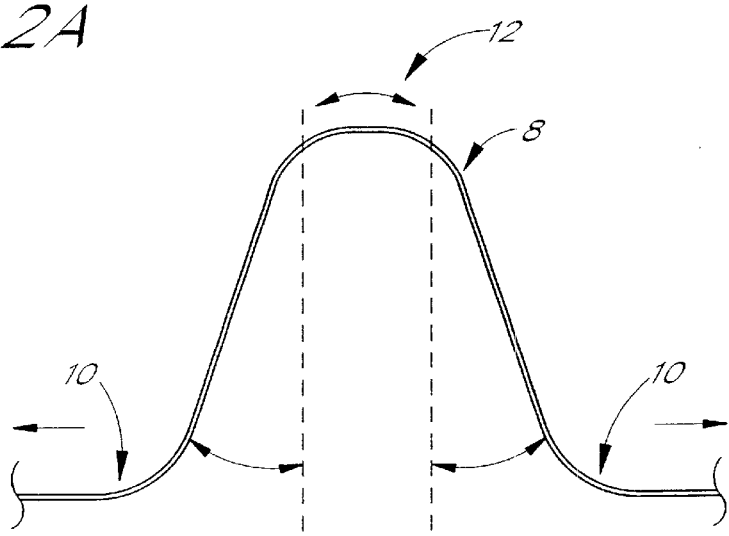
Figure 2C:
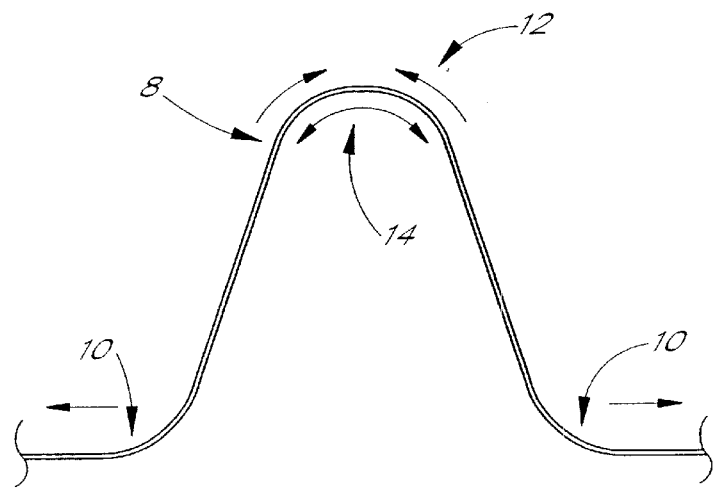
Figure 3:
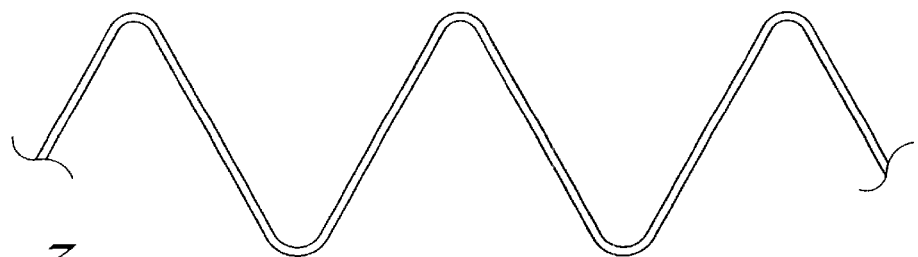
FIG. 3 illustrates V-shaped bending hinges.
Figure 4:
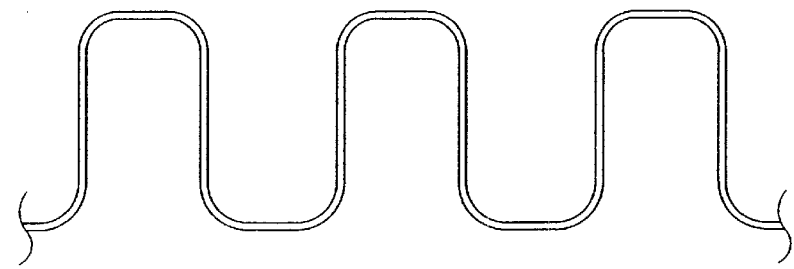
FIG. 4 illustrates U-shaped bending hinges.
Figure 5:
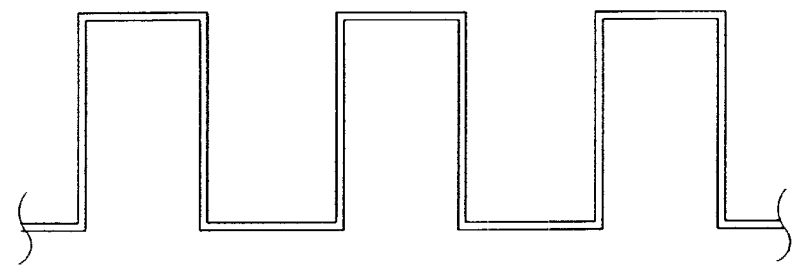
FIG. 5 illustrates square-wave-shaped bending hinges.
Figure 6:
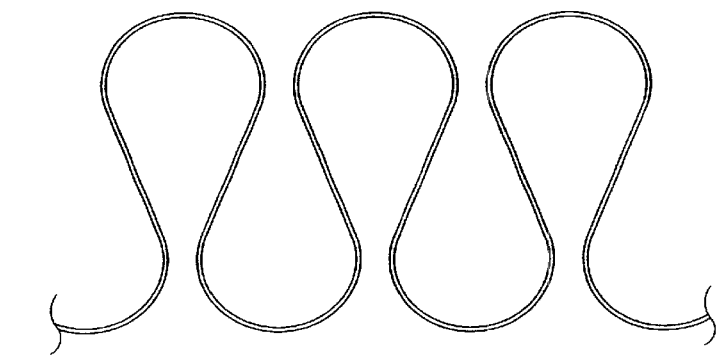
FIG. 6 illustrates teardrop-shaped bending hinges.
Figure 7:
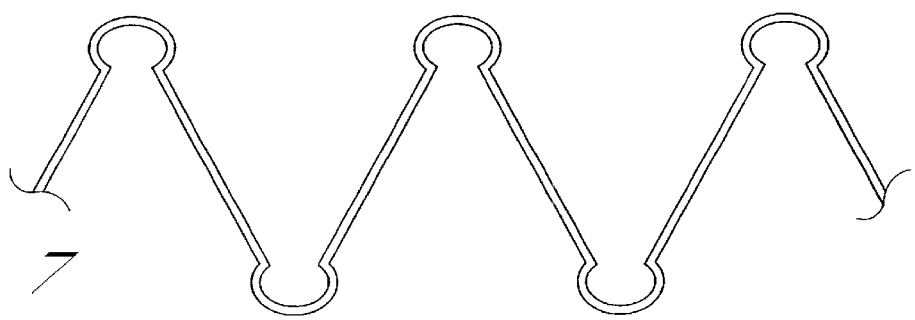
FIG. 7 illustrates keyhole-shaped bending hinges.

Each hinge 6 provides unidirectional elasticity, in that it acts in one direction and does not provide much elasticity in the direction perpendicular to that direction. FIGS. 2a–2c illustrate a preferred embodiment of the elastic hinge. FIG. 2a illustrates how the hinge 6 can be generally U-shaped with a central portion 8 that has at least one inner and outer radius of curvature, and two arms 10 extending from the central portion 8. The two arms 10 are aligned to be roughly perpendicular to the primary direction of elasticity. The components of the hinge 6 lie flat in a plane parallel to the surface of the epicardium. Thus, when the ventricle dilates in congestive failure, the ends of the arms 10 are pulled away from each other, as illustrated in FIG. 2b. This imposes a bending moment on the central portion 8. Mechanically, this creates a state in which there is compression on the outside of the bend 12 and tension on the inside of the bend 14 in the central portion 8 of the hinge 6. These compressive 12 and tensile 14 regions are separated by a neutral axis. The stresses can be distributed differently by varying the shape of the central portion 8. For example, as illustrated in FIGS. 3–7, the hinges 6 can be V-shaped (FIG. 3), U-shaped (FIG. 4), square-wave-shaped (FIG. 5), teardrop-shaped (FIG. 6), or keyhole-shaped (FIG. 7). The deformation and bearing of the load in the hinge structure 6 is taken up primarily by the bending of the central portion 8 and the arms 10. Little load is carried in pure tension parallel to the wire direction.

An advantageous feature is that the hinges 6 are designed such that the elastic limit or yield point of their material is not exceeded during use. In other words, the hinges 6 operate in their elastic range so that they can recover to their original, stress-free configuration when they are unloaded. In addition, an important aspect to the use of a harness 4 comprised of elastic hinges 6 is that the harness 4 is sized such that it remains in elastic, compressive contact with the heart 2.

Another advantageous characteristic of the elastic bending hinges 6 is that they apply increasing resistive force with increasing bending. The more they are stretched, the greater force with which they resist. Overall, a harness 4 constructed of these hinges 6 will behave in a similar fashion. A goal of cardiac or left-ventricular harnessing according to the preferred embodiment is to apply a gentle compressive pressure against the surface of the epicardium of the heart 2. As the left ventricular wall distends locally or globally, it will be met with increasing pressure by the hinges 6, locally or globally. Increased pressure exerted by the harness 4 lowers wall stress within the left ventricle and thus may prevent further infarct expansion, global dilatation, and remodeling. The cardiac harness 4 according to the preferred embodiment mechanically resists size and shape changes that take place in the heart 2 after an acute myocardial infarction. In addition, the harness 4 may be capable of reversing the remodeling process that occurs post-infarction. If reverse remodeling occurs, and the left ventricular shape and size consequently decrease back toward normal, then resistive pressure from the harness 4 will commensurately decrease, as well.

One of the most effective means of limiting infarct expansion and preventing the onset of the remodeling process after an acute myocardial infarction is revascularization of infarcted and jeopardized myocardium. Most often this is achieved by coronary artery bypass grafting. The application of a cardiac harness according to the preferred embodiment during bypass grafting can provide further benefit. The myocardial sparing effect of the harness, by decreasing wall tension, has been shown experimentally to reduce myocardial energy consumption and therefore reduce myocardial oxygen demand. If a bypass graft should become stenosed over time and cause the myocardium to become ischemic, the harness may attenuate any remodeling that might result. In addition to being an accompaniment to coronary artery bypass grafting, application of the cardiac harness might occur at the time of aortic or mitral valve repair or replacement surgeries.

Hinges 6 can be disposed in helical elements, also referred to in this discussion as rings 80, rows, or strips 20, around the circumference of the left ventricle or the heart. Strips 20 can contain one or more connected hinges 6. Hinges 6 in a strip 20 are oriented to have the same axis of elasticity as other hinges 6 in a strip 20. Strips 20 can be joined or they can be independent of one another. As shown in FIGS. 8a–8e, strips 20 of hinges 6 can be joined by interconnecting elements 16 in a variety of ways. For example, an interconnecting element 16 can join the arm portion of one hinge 6 within a first strip 20 to a central portion 8 of a hinge 6 in a second strip 20.

Figure 8A:
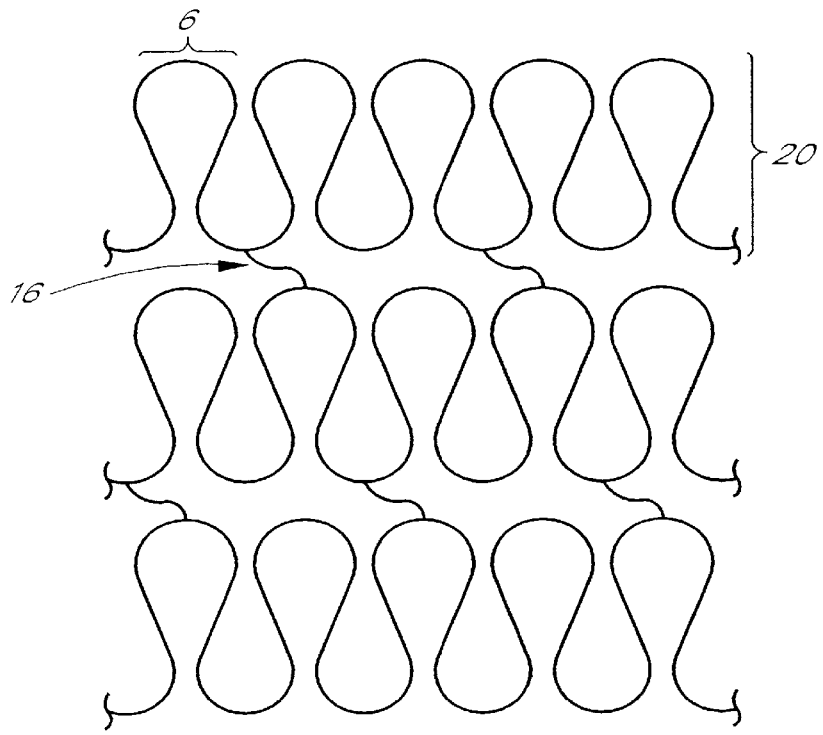
FIGS. 8A–8E illustrate various types of interconnections between strips or rows of bending hinges.
Figure 8B:
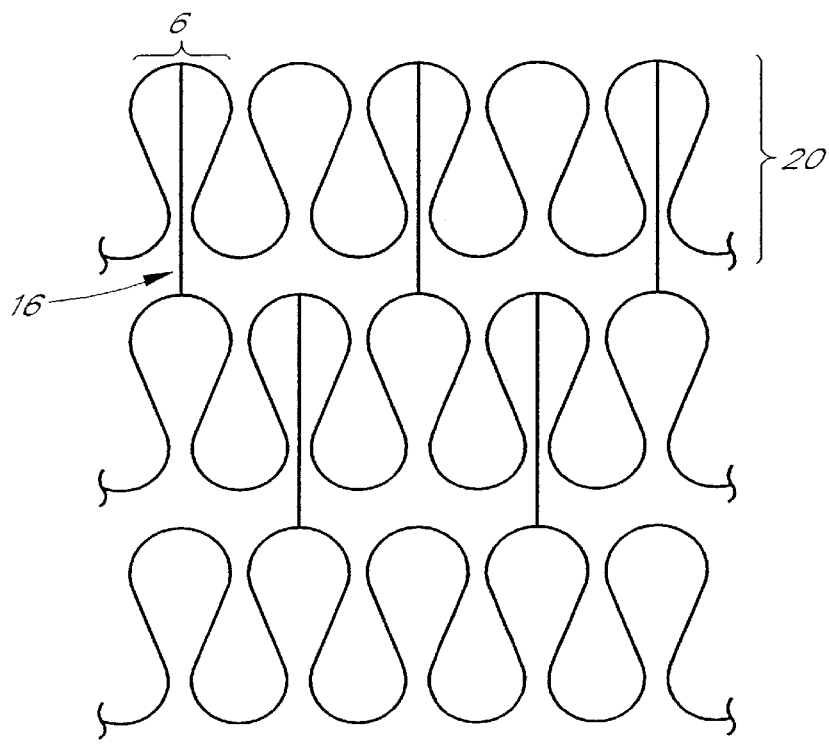
Figure 8C:
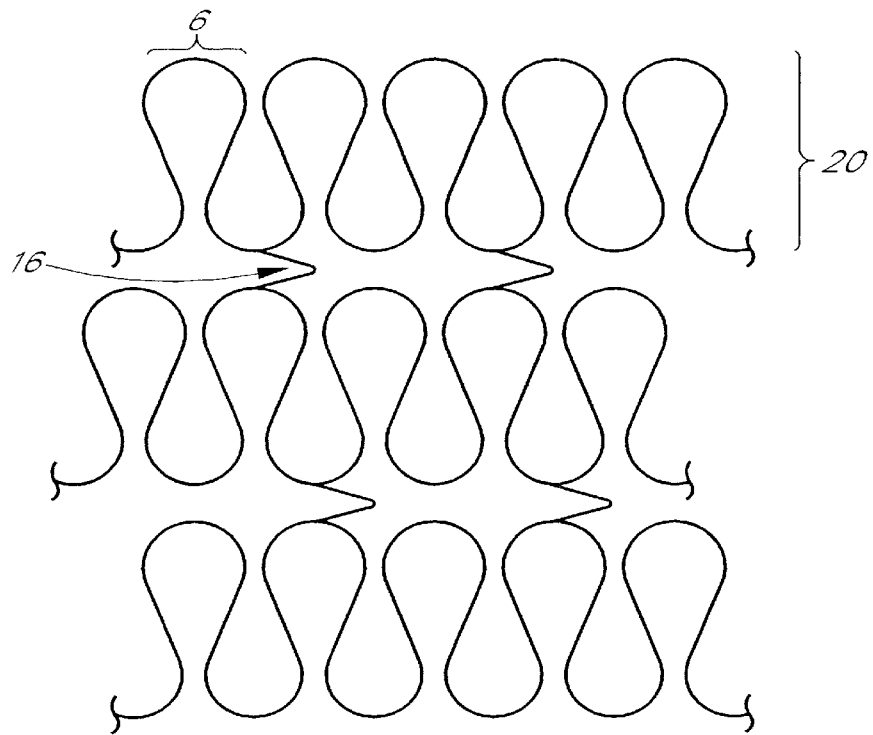
Figure 8D:
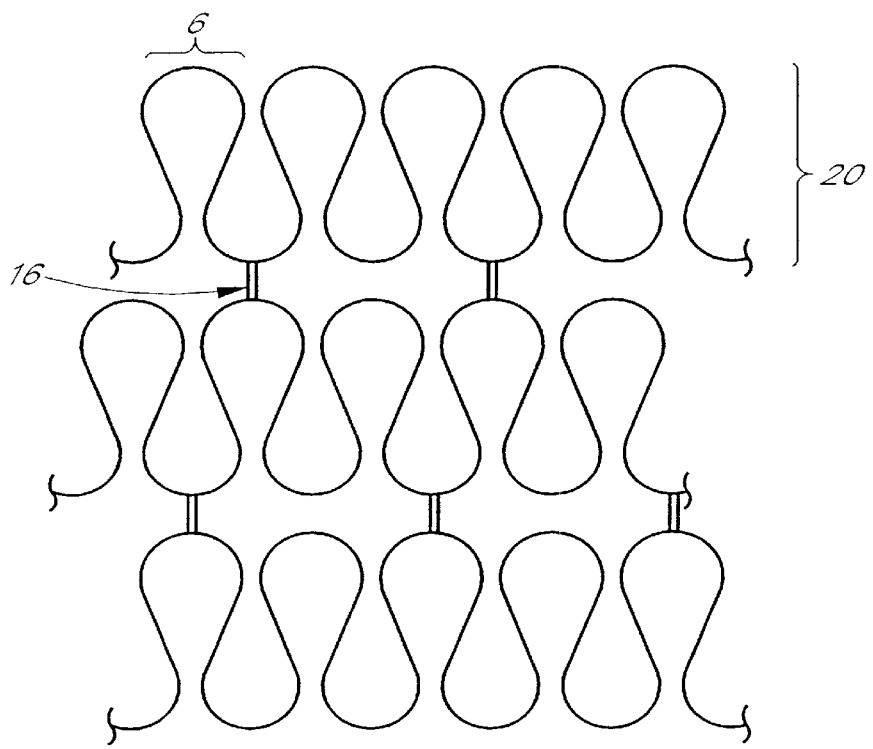

In FIG. 8b another configuration is illustrated. The central portion of a hinge 6 within a first strip 20 is joined to the central portion of another hinge 6 in a second strip 20, by an interconnecting element 16. As illustrated in FIG. 8c, the interconnecting element 16 can be angled to provide a spring-like mechanism between strips 20. FIG. 8d shows another configuration of the interconnecting element 16, providing firmer support between hinges 6 in different rows 20.

Joined strips 20 can be linked by longitudinally oriented hinges 18 which act as interconnections between strips 20. These longitudinally oriented hinges 18 provide elastic recoil in the longitudinal direction, while the strips 20 of hinges 6 provide the usual elasticity in the transverse direction. This arrangement imparts a more isotropic elastic structure than the previously described embodiments.

Figure 9A:
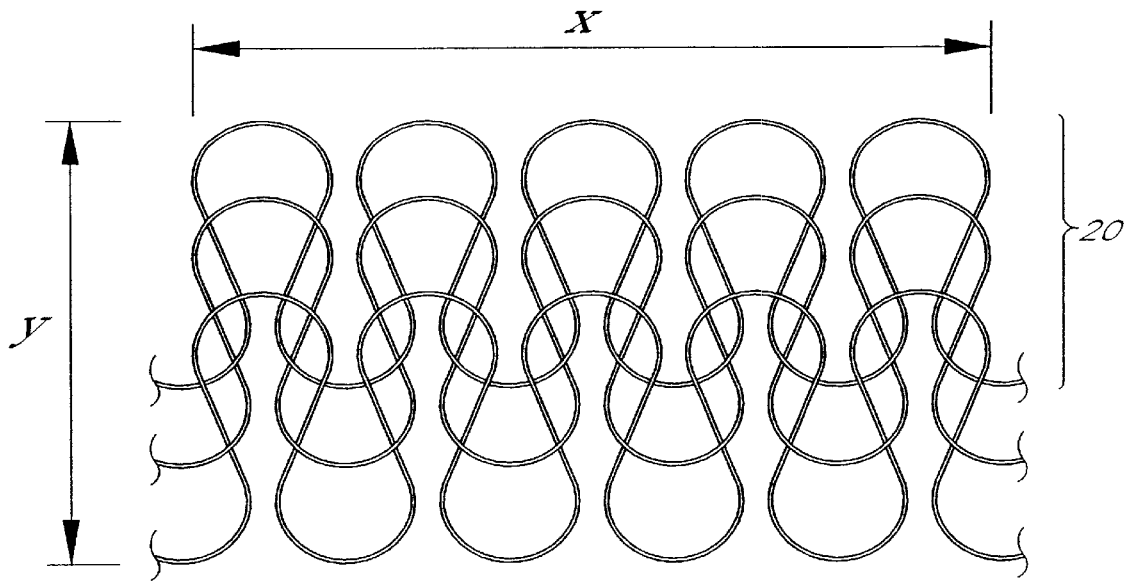
FIGS. 9A–9C illustrate the principle of decoupling of longitudinal expansion from transverse expansion of bending hinges.
Figure 9B:
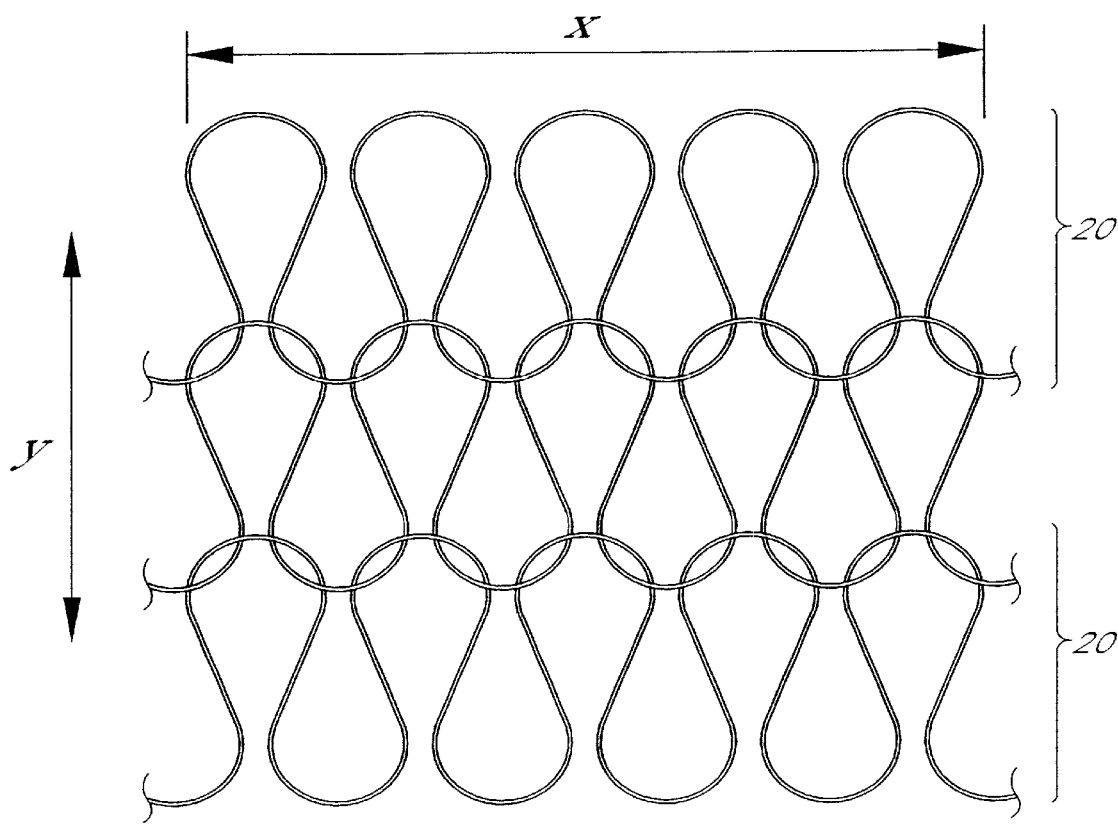
Figure 9C:
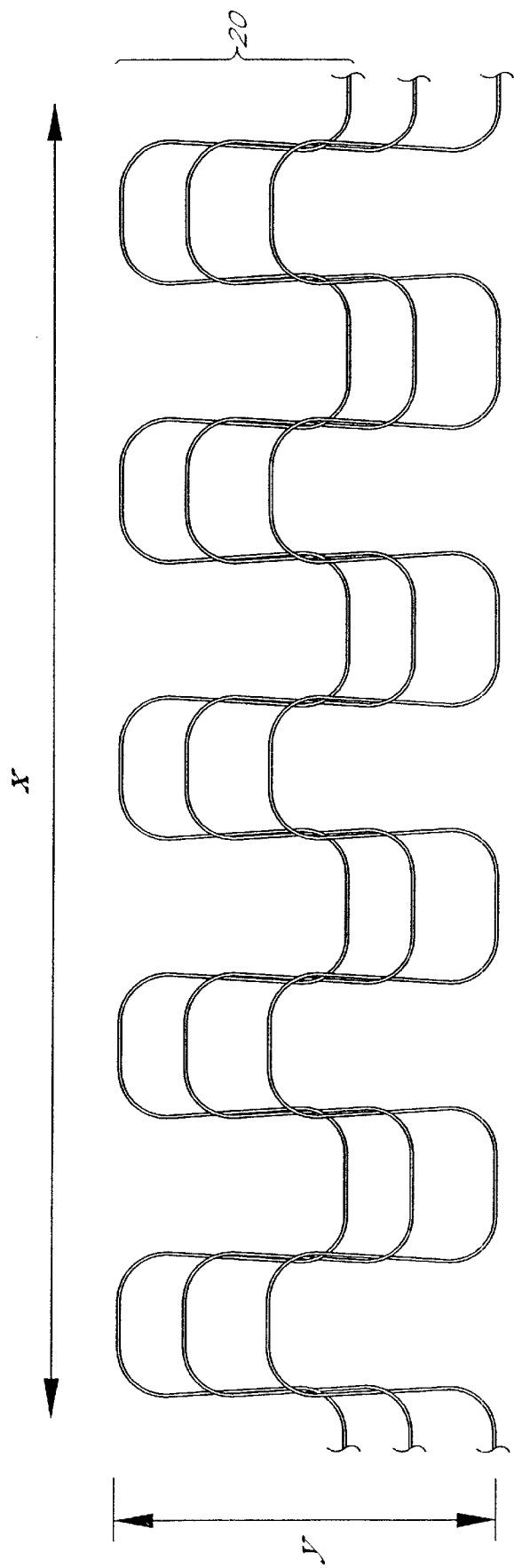

An advantageous feature of the preferred embodiment is the decoupling of the action of the harness in the circumferential or transverse dimension from the longitudinal direction. This decoupling is accomplished by allowing a hinge 6 to stretch or bend circumferentially, or transversely, without pulling much longitudinally on the adjacent hinges. This principle is illustrated in FIGS. 9a–9c. The relaxed, or end-systolic, configuration of the rows or strips 20 of hinges 6 is shown in FIG. 9a. There is considerable longitudinal overlap between the hinges 6 from one strip to another. In FIG. 9b, one can see that by pulling the strips apart in the longitudinal direction (along the Y axis), there is a little or no foreshortening of the strips 20 of hinges 6 in the transverse direction (i.e., along the X axis). This lack of foreshortening in the X axis is due to the fact that pulling apart the strips 20 of hinges 6 in the Y direction produces very little compression of the hinges 6.

FIG. 9c illustrates a corollary property of the hinges 6, most readily seen when the cardiac harness 4 is applied to a live heart 2: The stretching of the strips 20 of hinges 6 in the transverse (X-axis) direction produces very little or no foreshortening in the longitudinal (Y-axis) direction. In the region of the cardiac base, which is close to the outflow (aortic and pulmonic) valves, it is advantageous to have the rows 20 of hinges 6 expanding and contracting in the circumferential or transverse direction (i.e., along the X axis) while little or no foreshortening in the longitudinal direction (i.e., along the Y axis) occurs. This phenomenon is illustrated in FIG. 9c. Closer to the cardiac apex, it may be more advantageous to have the rows or strips 20 of hinges 6 move apart in the longitudinal direction (i.e., along the Y axis) while there is very little or no foreshortening in the circumferential or transverse direction (i.e., along the X axis). This phenomenon is illustrated in FIG. 9b.

Figure 8E:
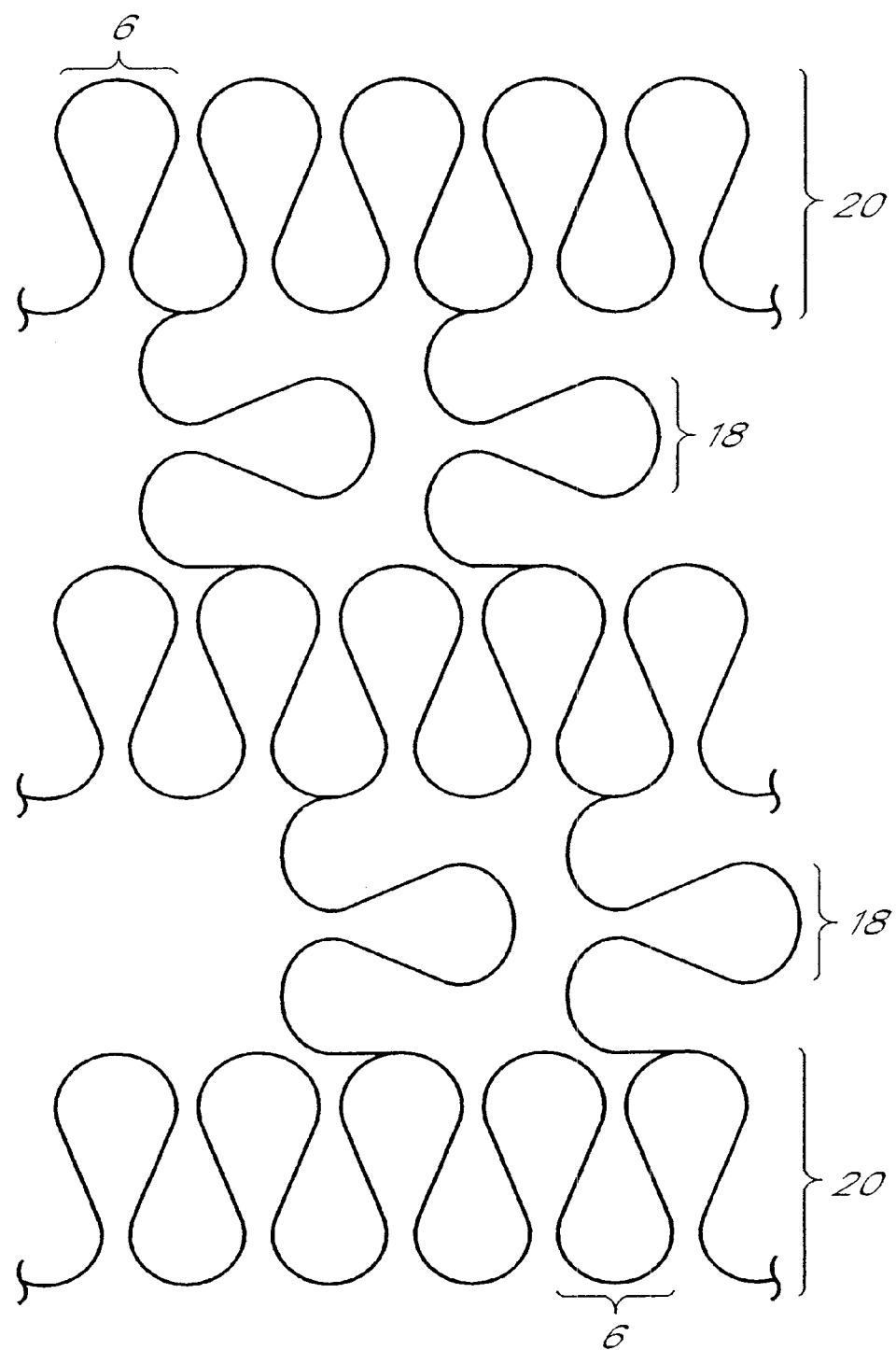

An additional way that the longitudinal expansion of the harness can be decoupled from the transverse expansion of the harness is through the use of elastically recoiling interconnecting elements 16, as illustrated in FIGS. 8a and 8c. Additionally, having interconnecting hinges 18, as illustrated in FIG. 8e, is, an additional way of decoupling longitudinal contraction and expansion of the harness from transverse expansion and contraction of the hinges 6 within the harness 4.

Figure 10A:
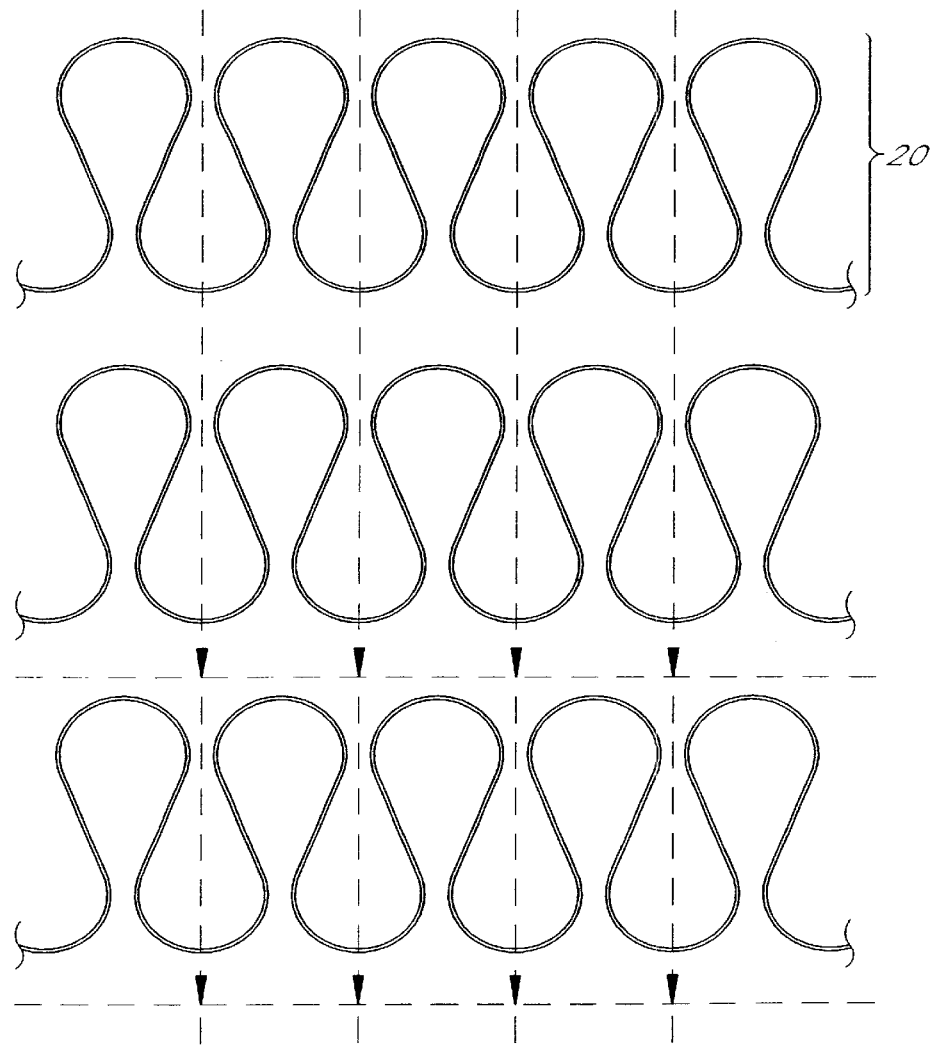
FIGS. 10A–10B illustrate interlocking of rows of bending hinges.
Figure 10B:
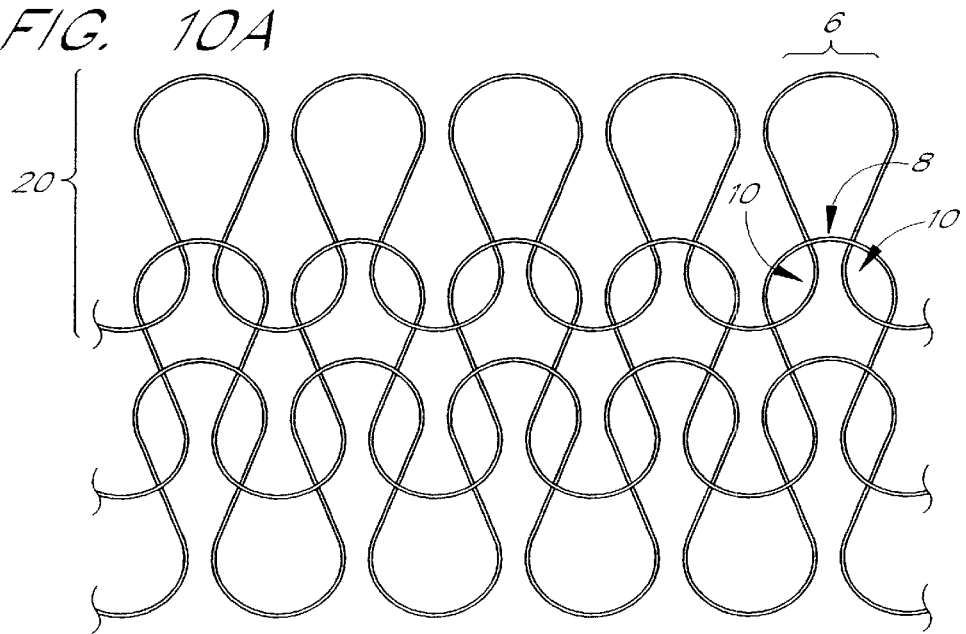
Figure 11A:
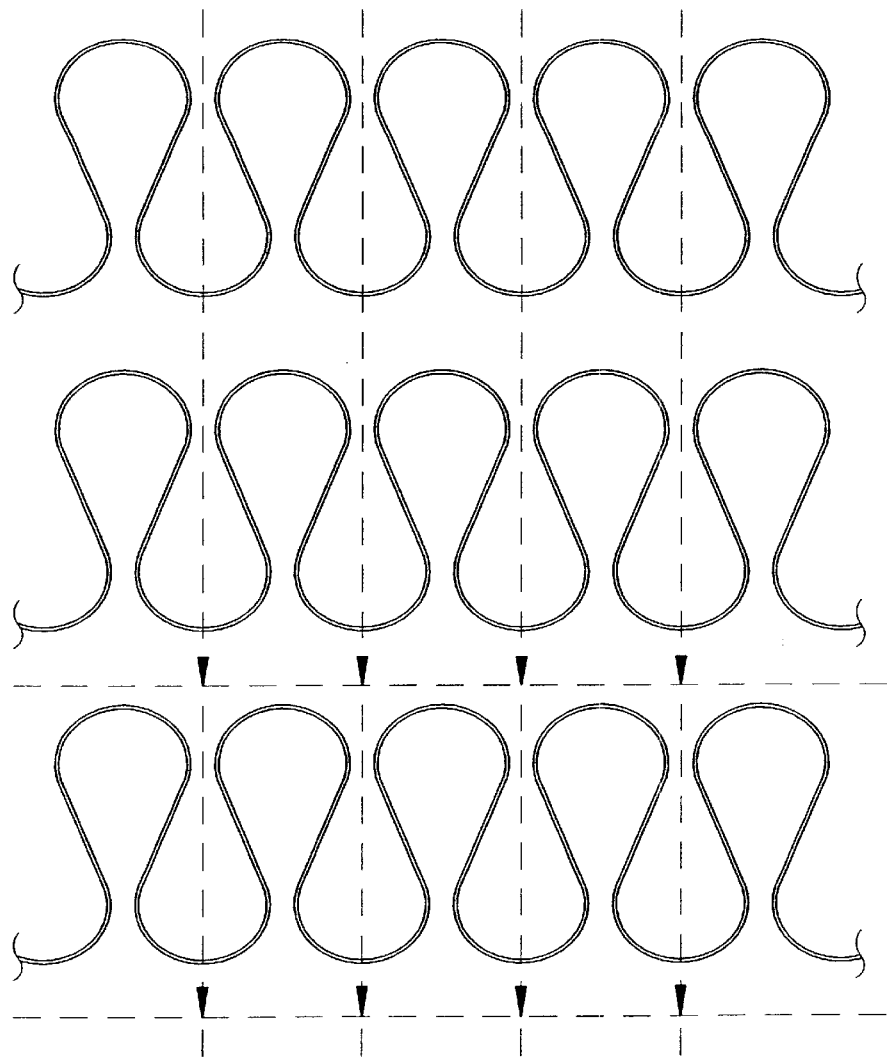
FIGS. 11A–11B illustrate interweaving of rows of bending hinges.
Figure 11B:
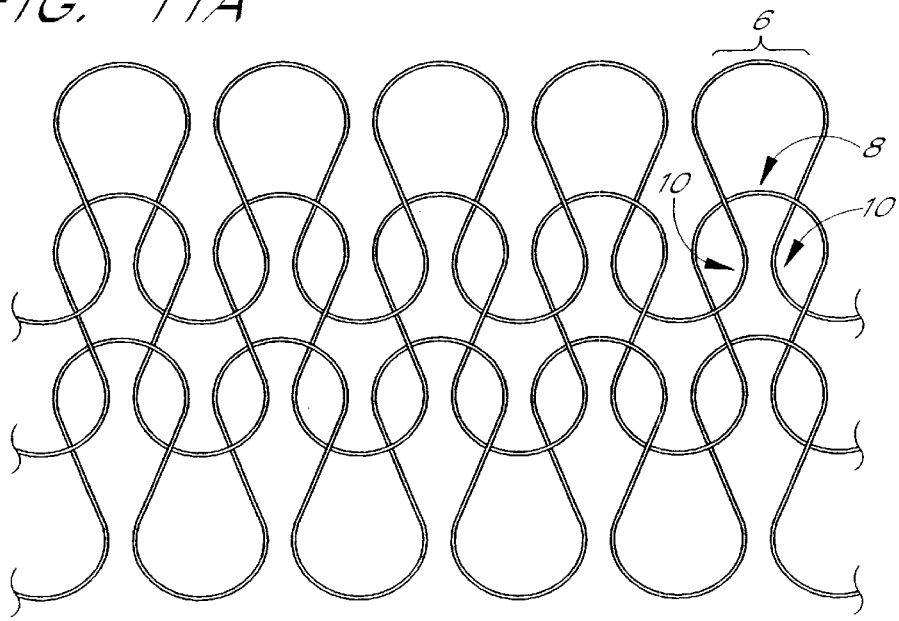

Alternatively, as illustrated in FIGS. 10 and 11, the rows or strips 20 of hinges 6 can be interlocked (FIGS. 10a and 10b) or interwoven (FIGS. 11a and 11b). To interlock strips 20 of hinges 6, the central portion 8 of a hinge 6 from a first row, or strip 20, is placed between the arms 10 of a hinge from a second row. This placement of a "hinge within a hinge" occurs for one or more hinges 6 in a first strip 20, relative to the hinges in a second strip. To interweave strips 20 of hinges 6, as illustrated in FIGS. 11a and 11b, the strips 20 are configured such that one arm 10 of a first hinge 6 from a first strip 20 lies under the central portion 8 of a second hinge from a second strip, while the other arm 10 of the first hinge 6 lies over the central portion 8 of the second hinge from the second strip.

Another embodiment comprises a variable hinge network (not illustrated). In this network, hinges within a strip vary in height. Thus, a short hinge may be followed by a tall hinge, followed by a short hinge, and so on within a strip. This variable hinge network provides the capability to tailor the stiffness of the harness such that the stiffness varies with the degree of stretch. For example, at some first threshold of distension, the tall hinges deform, and at some higher threshold of distension, the shorter hinges, which are stiffer, begin to deform. This arrangement can advantageously provide a pressure-versus-diameter curve for the harness that exhibits two distinct stiffness peaks at different diameters—with diameter corresponding to ventricular wall stretch or degree of distension.

An important difference between the decoupled hinge harness construction of the preferred embodiment and a knitted fabric harness, or cardiac "sock," is the hinge harness's ability to closely track changes in sphericity of the underlying heart, whether the heart is healthy or diseased. This has been demonstrated experimentally by using an inflated latex bladder, which simulates a heart in its expansion and contraction. First, relative changes in sphericity of the bladder were measured. Note that sphericity is defined as diameter (D) divided by length (L):

$$sphericity = \frac{diameter}{length}$$

Figure 12:
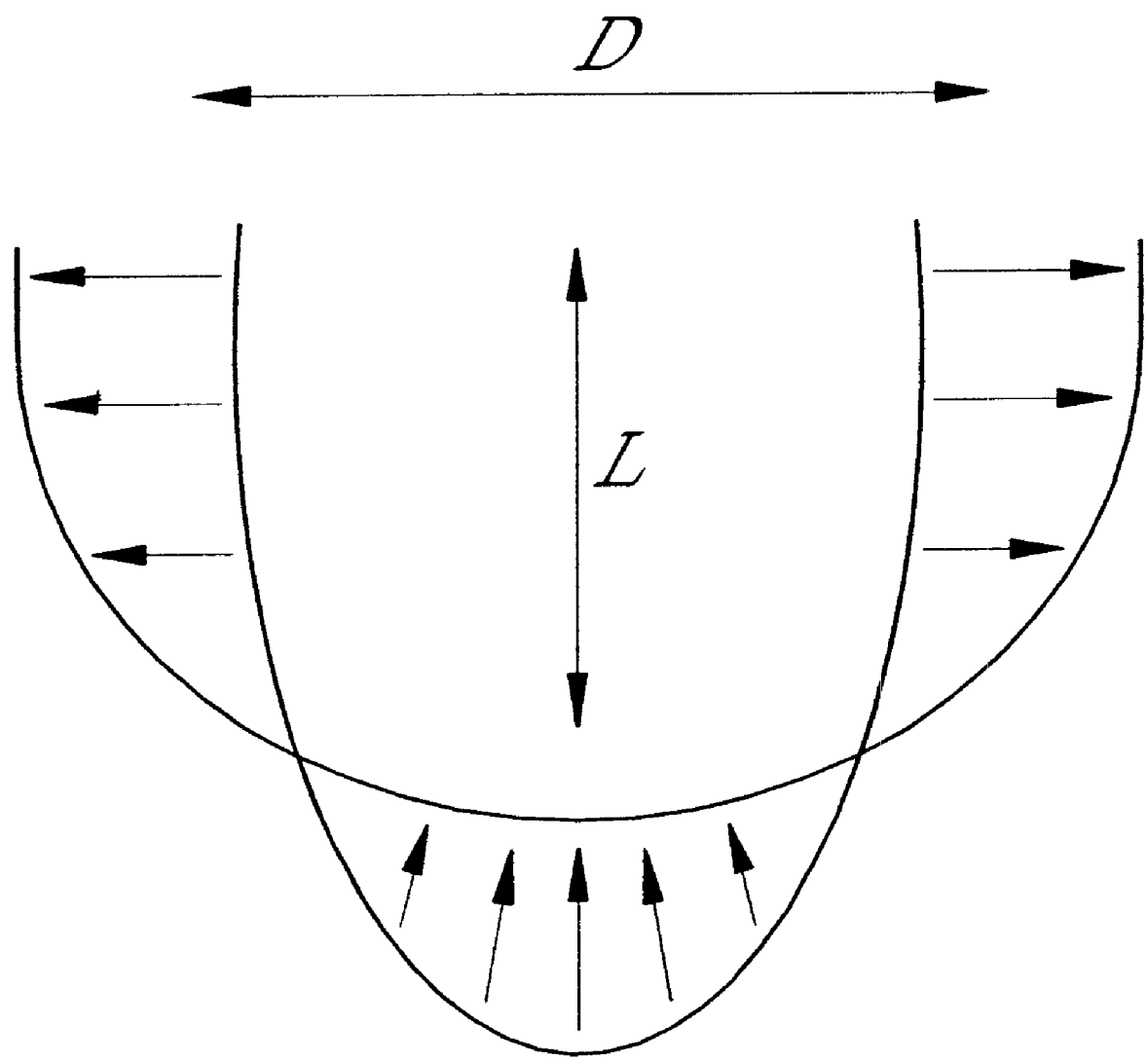
FIG. 12 is a schematic illustration of the diameter and length dimensions of the cardiac wall.
Figure 13:
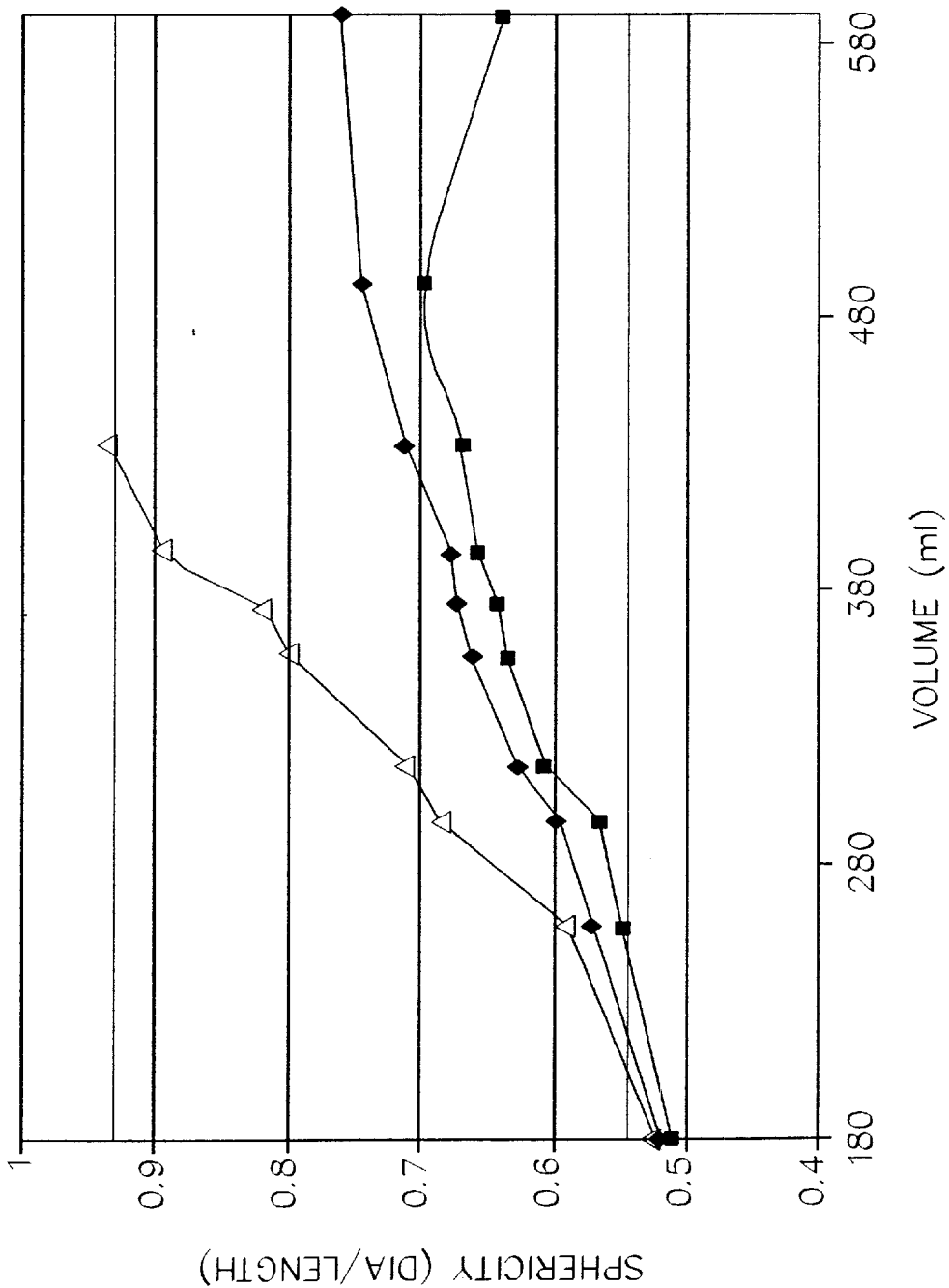
FIG. 13 is a graph of the sphericity-versus-volume relationship of a latex bladder: alone, in conjunction with application of the cardiac harness, and in conjunction with application of a polyester knit'sock.

This relationship is illustrated in FIG. 12, which shows the diameter (D) of the heart in the transverse dimension and the length (L) of the heart in the longitudinal direction. The results of this experiment are illustrated in FIG. 13. When the bladder was inflated alone (i.e., without the presence of a harness), it generated a sphericity-versus-volume curve that is illustrated as the middle curve in FIG. 13. When a polyester knit "sock" was applied to the bladder, there was a great increase in sphericity as the volume of the bladder increased, as illustrated by the top curve of FIG. 13. In contrast, when the elastic hinge harness 4 of the preferred embodiment was applied to the bladder, the sphericity-versus-volume curve more closely matched that of the unencumbered bladder alone. The elastic hinge harness sphericity curve is illustrated as the bottom curve in FIG. 13. Thus, the elastic hinge harness of the preferred embodiment closely tracks changes in sphericity over a range of volumes of the underlying structure, in this case a latex bladder. The nonforeshortening elastic hinge harness 4 had little impact on the sphericity index as bladder volume increased. In fact, the sphericity index values were slightly lower than for the bladder alone. In contrast, the presence of the knitted sock significantly increased the sphericity of the bladder as its volume was increased. This demonstrates the potential importance of the nonforeshortening elastic feature of the harness with respect to its application to the human heart. The harness has the ability either (1) to "track" (i.e., minimally alter) changes in sphericity of one or both ventricles throughout systole and diastole; or (2) to progressively decrease the sphericity index of the heart, relative to an unencumbered heart (i.e., without the harness), as diastole proceeds, whether the heart is healthy or in congestive failure.

The hinges 6 can be made of a variety of materials, including metals, polymers, composites, ceramics, and biologic tissue. Specific materials include stainless steel, Elgiloy, titanium, tantalum, Nitinol, ePTFE, collagen, nylon, polyester, and urethane. Advantageously, the hinges are made from a metal, particularly Nitinol, because metals have a higher Young's modulus or stiffness, than polymers or tissue. This allows less mass and volume of material to be used to achieve the same mechanical reinforcing strength. Prosthetic materials that are directly applied to the epicardium, especially if there is some relative movement between the epicardium and the material, can induce fibrosis, which is marked by collagen deposition leading to scarring. Consequently, an implant with less surface area in contact with the epicardium tends to generate less fibrosis on the surface of the heart. Excessive fibrosis can lead to a constrictive pericarditis and, ultimately, to elevated venous pressures with disastrous consequences.

Nitinol is especially suitable for the construction of the harness 4. It has the advantageous capability of being able to remain elastic over a great range of strain, up to 4%, which is greater than other metals. It generates a relatively benign foreign body response from tissue, and it is relatively magnetic-resonance-imaging-compatible, as it is not highly ferromagnetic. Nitinol is also corrosion- and fatigue-resistant. In addition, metal such as Nitinol are more creep-resistant than polymeric or tissue-based materials. In a passive elastic harness application, hinge 6 would be formed in an austenitic state at body temperature when no load is applied and the material is in a stress-free state. When the harness is placed on the heart, the contact pressure between the harness and the heart may stress-induce martensite within the otherwise austenitic structure.

The hinge elements can be made from wire, or they may be machined from sheet or tubing material, or a combination of these. In order to make such a structure out of Nitinol wire, the wire is wound and constrained in the desired configuration. It is then annealed at approximately 470° C. for approximately 20 minutes to set the shape. Alternatively, Nitinol tubing can be machined with a laser to create the desired structure. Another alternative is the photochemical etching of sheets of Nitinol. In both of these latter methods, a subsequent annealing can be performed.

Figure 14:
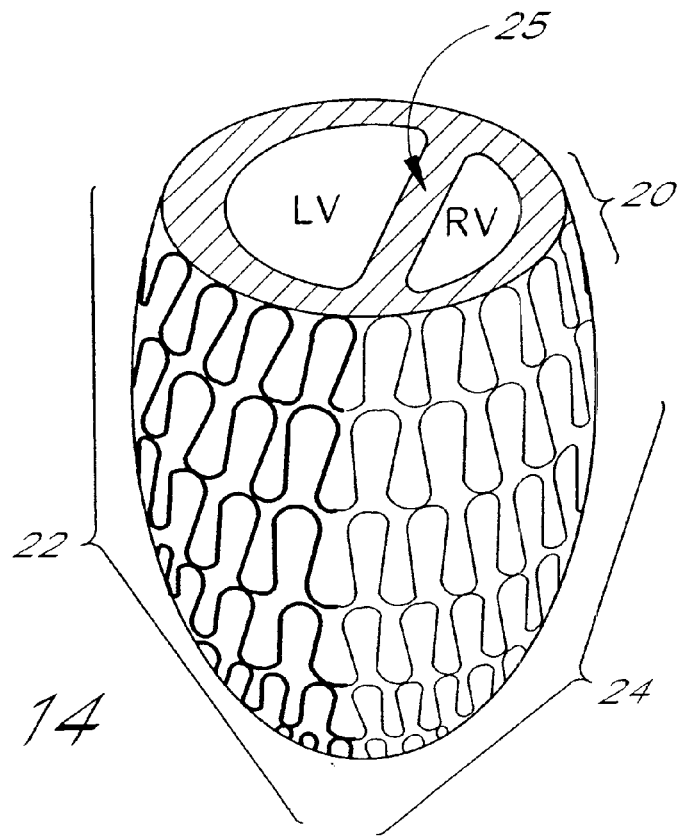
FIG. 14 is a schematic diagram of the cardiac harness in place on the heart, with stiffer, thicker hinges covering the left ventricle than the right ventricle.

In addition to varying the direction of elastic support, the extent of support or stiffness can be varied as well. Hinges of different shape or of different material dimensions can accomplish this. Because of the difference in compliance between the left and right ventricles, it can be desirable to have the left side of the harness stiffer than the right side. This can be achieved in several ways. A harness structure can be constructed with stiffer hinges against the surface of the left ventricle than the right, as illustrated in FIG. 14. The hinges covering the left ventricle 22 are thicker, smaller, or otherwise stiffer than the hinges covering the right ventricle 24. Also shown in FIG. 14 are the individual strips 20 of hinges, as well as the interventricular septum 25, between left ventricle (LV) and right ventricle (RV).

In a preferred arrangement, a wire or plastic frame comprising two struts (not illustrated) can be integrated with the harness 4. The frame acts similarly to a clothespin, in that it exerts a clamping pressure along vectors 180 degrees apart, limiting the amount the ventricle(s) are allowed to distend. The amount of pressure exerted by the frame can be adjusted by making the frame larger or smaller, or thicker or thinner. The harness can also feature more than one frame. The harness's hinges 6 positioned between the wire frames, or between struts of frames, can be of varying thickness or size to apply varying stiffness and to allow for more or less ventricular distension.

Figure 15:
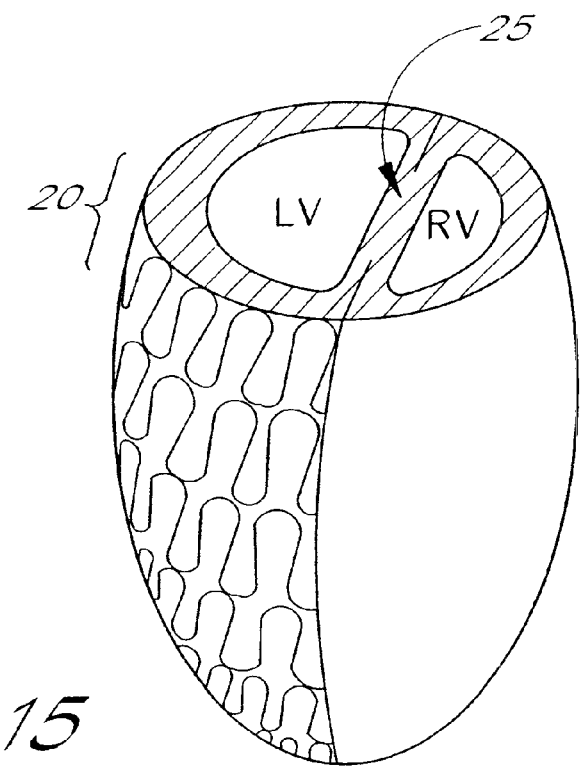
FIG. 15 is a schematic diagram of the cardiac harness applied only to the left ventricle.

In another embodiment, illustrated in FIG. 15, the cardiac harness may be selectively applied to only the left ventricle (or the right ventricle), depending on which side of the heart is most diseased. In this illustration, the cardiac harness is applied to the left ventricle because the left ventricle fails far more often than the right ventricle. The harness may be anchored to the left ventricle in a variety of ways, including having anchoring struts that extend into the interventricular septum 25, as shown in FIG. 15.

Advantageously, most or all of the surface of the left ventricle is covered by the harness 4. This ensures maximum reinforcement both globally, to attenuate global shape change and dilatation, and locally, to prevent ventricular wall thinning and stretch in an infarcted area. Note that this is not to say that the actual surface area of the harness in contact with the epicardium needs to be large.

Figure 16A:
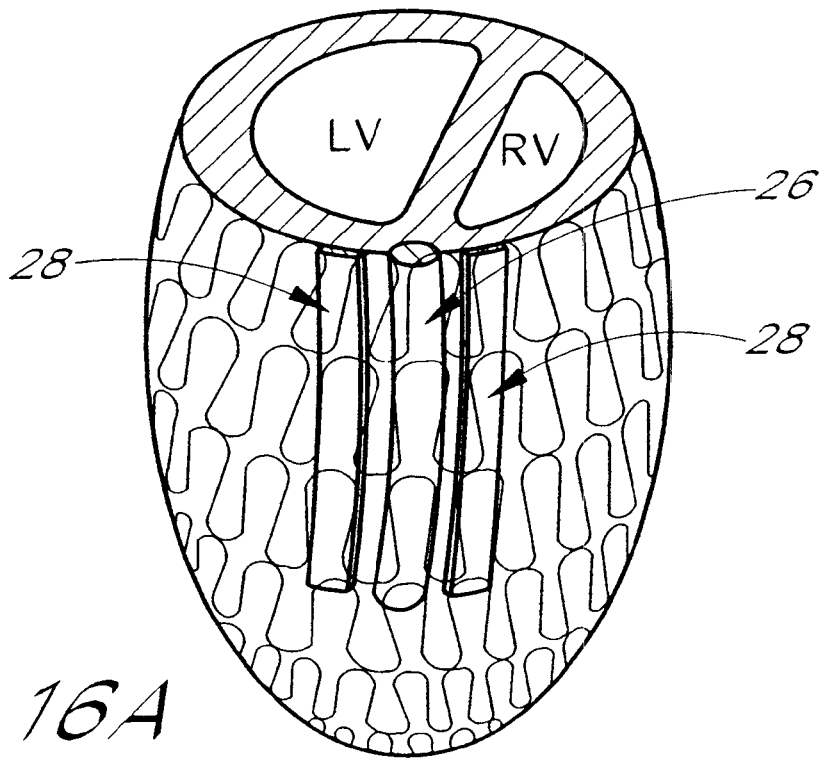
FIGS. 16A–16B demonstrate application of two protecting strips adjacent to a coronary artery, deep to the cardiac harness and superficial to the epicardium.
Figure 16B:
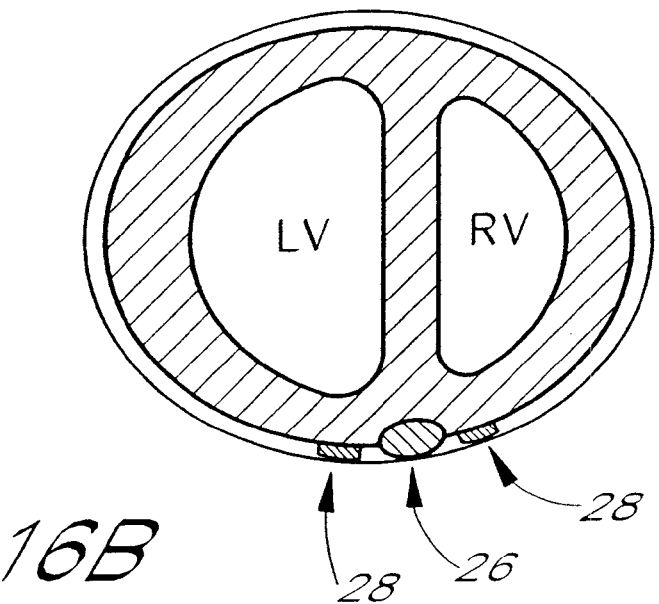

FIGS. 16a and 16b illustrate a protection mechanism for minimizing compression of one or more coronary arteries 26. To minimize the risk of ischemia, the compression of the harness on an epicardial coronary artery 26 can be alleviated by placement of protecting strips 28 on either side of the coronary artery 26. This mechanism lifts the harness 4 off of the coronary. artery 26. A suitable material for the protecting strip 26 can be expanded polytetrafluoroethylene ePTFE.

Figure 17:
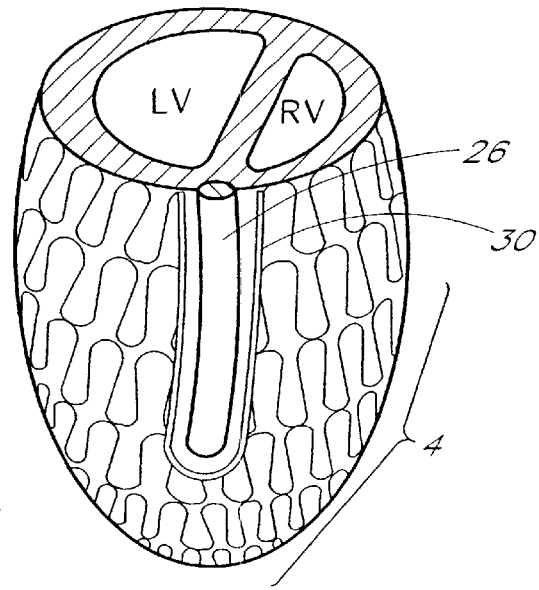
FIG. 17 is a schematic diagram of a wire frame attached to the cardiac harness and surrounding a coronary artery.

Another approach to minimizing compression of the coronary artery 26 is illustrated in FIG. 17. A wire frame 30 that runs parallel to the coronary artery 26 can be integrated into the harness 4. The hinges 6 can be suspended from the wire frame 30 like curtains on a curtain rod. The hinges 6 extend from one arm of the wire frame 30 to 30 the other over the surface of the myocardium, between coronary arteries.

Advantageously, the compliance of the elastic harness 4 is in the range of compliance of native pericardium or latissimus dorsi muscle wraps. Preferably, the compliance of the harness 4 increases gradually as a function of stretch. Over the operational range of the harness, compliance should not fall so low that the harness 4 becomes constrictive. Therefore, the pressure exerted on the heart 2 by the harness 4 preferably does not exceed 10 mm Hg. However, if only the left ventricle is reinforced by the harness 4, then greater pressures are possible without causing constrictive conditions.

Figure 18A:
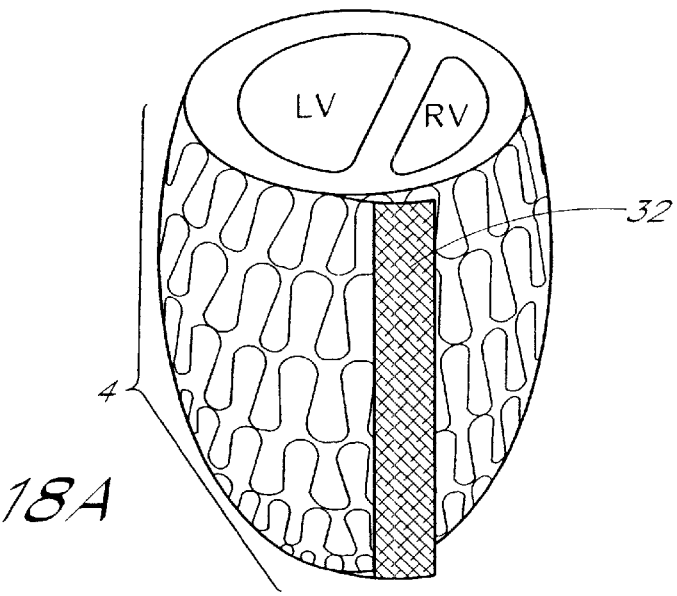
FIGS. 18A–18B are schematic illustrations of a wraparound embodiment of the cardiac harness, with a fastening strip applied to the leading edge of the cardiac harness.
Figure 18B:
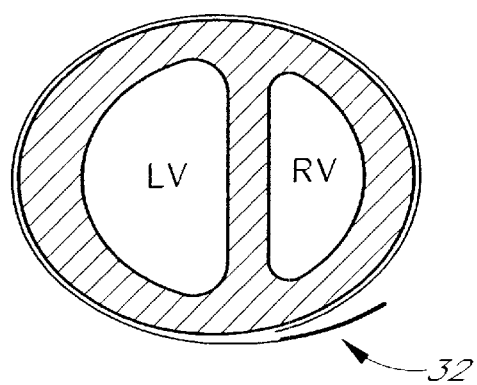

Various designs incorporating decoupled hinges 6 are possible. The hinges 6 can wrap continuously around both ventricles or just around the left ventricle or right ventricle. The harness 4 can have a seam for size adjustment, or it can be of a one-size-fits-all design. A Nitinol harness can be provided presized to fit the dimensions of a patient's heart. Alternatively, the harness components can be provided in a kit that a surgeon can custom-assemble in the operating room, based on sizing information gained before or at the time of surgery. A kit can consist of modular components that can be assembled quickly. The use of hinge strips 20 that are ring-shaped and of varying diameters and stiffness is one possibility. The surgeon can interlock hinges 6 between adjacent hinge strips 20 in order to couple the strips 20, as illustrated in FIG. 10b. Precise sizing can be facilitated by using a belt buckle or adhesive fastener (e.g., a hook-and-loop fastener, such as Velcro™) type of design, as illustrated in FIGS. 18a and 18b. FIGS. 18a and 18b illustrate the harness 4 wrapped around the heart 2, with a leading flap 32 that integrates an adhesive strip, such as Velcro™, for securing the harness 4 onto the heart 2. Such a design is not readily achievable using the knitted sock of previous designs.

Figure 19:
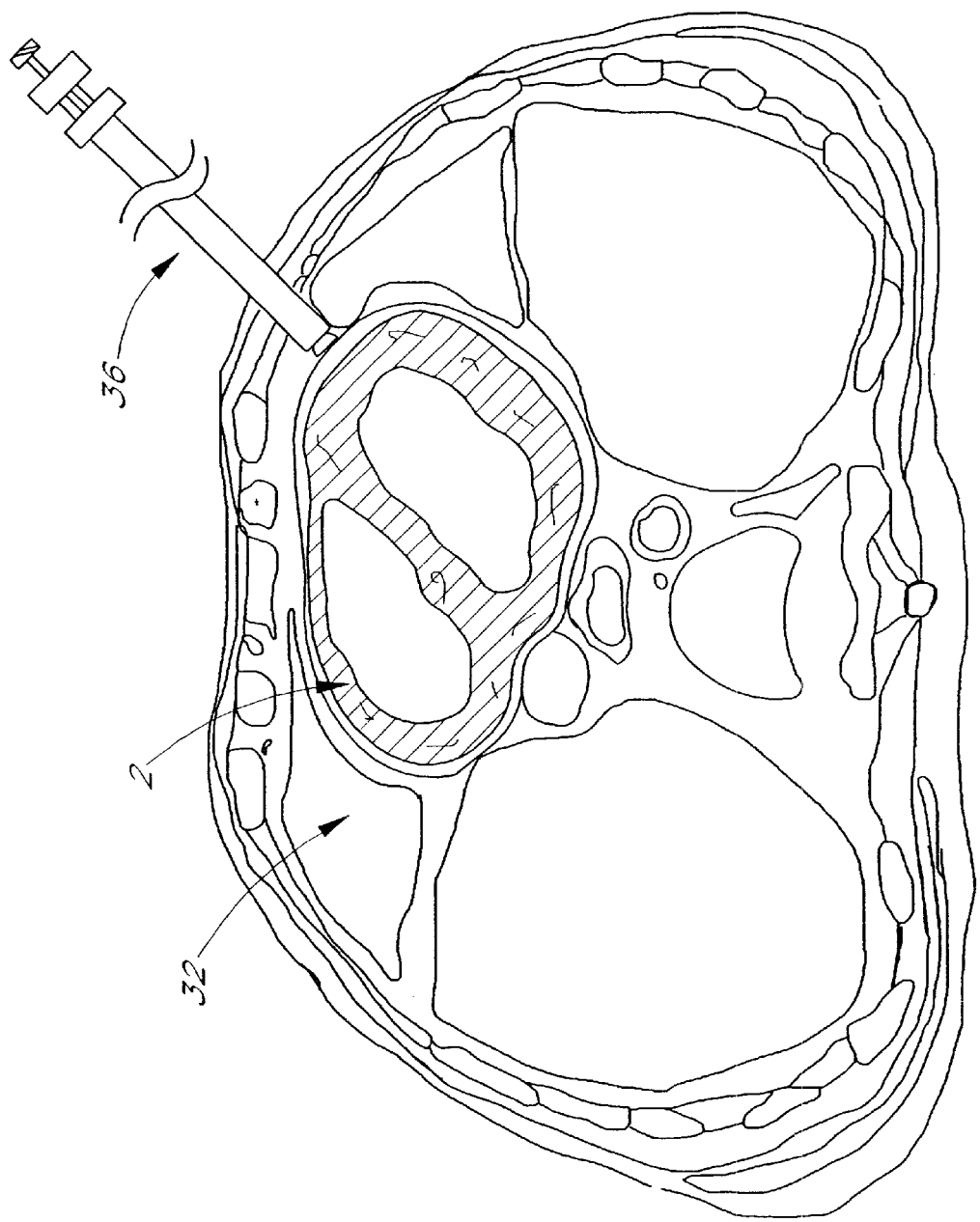
FIG. 19 is a schematic cross-sectional view of the human thorax with a cardiac harness delivery device inserted through an intercostal space and contacting the heart.
Figure 20A:
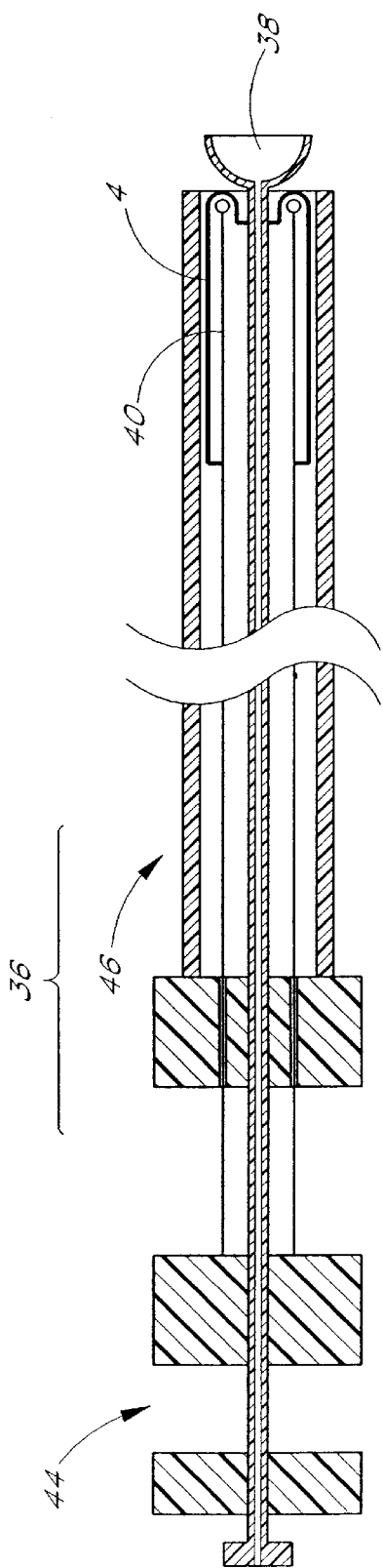
FIGS. 20–20B are cross-sectional elevational side views of a cardiac harness delivery device.
Figure 20B:
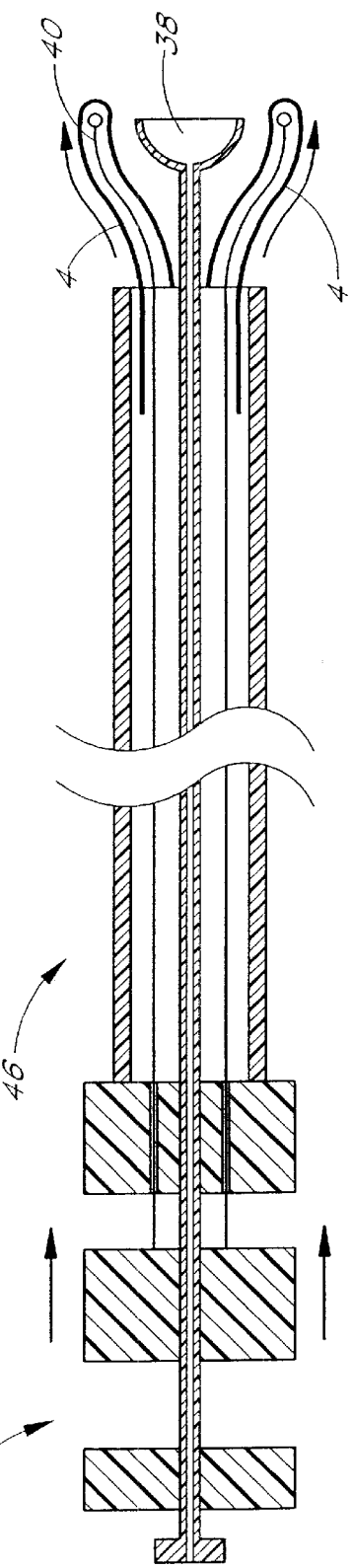

Delivery of the harness 4 can be accomplished through conventional cardiothoracic surgical techniques through a median sternotomy. Alternatively, the harness 4 may be delivered through minimally invasive surgical access to the thoracic cavity, as illustrated in FIG. 19. A delivery device 36 may be inserted into the thoracic cavity 34 between the patient's ribs to gain direct access to the heart 2. Preferably, such a minimally invasive procedure is accomplished on a beating heart, without the use of cardiopulmonary bypass. Access to the heart can be created with conventional surgical approaches. The pericardium may be opened completely, or a small incision can be made in the pericardium (pericardiotomy) to allow the delivery system 36 access to the heart 2. The delivery system 36 of the disclosed embodiments comprises an integrated unit of several components, as illustrated in FIGS. 20a and 20b. Preferably, there is a releasable suction device, such as a suction cup 38, at the distal tip of the delivery device 36. This negative pressure suction cup 38 is used to hold the apex of the heart 2. Negative pressure can be applied to the cup 38 using a syringe or other vacuum device. A negative pressure lock can be achieved through a one-way valve, stopcock, or a tubing clamp. The suction cup 38, advantageously formed of a biocompatible material, is preferably stiff to prevent any negative pressure loss through heart manipulation, this provides traction by which the harness 4 can be pushed forward onto the heart 2. In addition, the suction cup 38 can be used to lift the heart 2 to facilitate advancement of the harness 4 or allow visualization and surgical manipulation of the posterior side of the heart 2. After secure purchase of the apex of the heart 2 is achieved, the harness 4, which is collapsed within the body 46 of the delivery device 36, is advanced distally toward the heart 2 by actuating fingers 40. The harness 4 can be inverted (i.e., turned inside-out) ahead of time, to allow it to-unroll, or evert as it advances over the surface of the heart 2. In this discussion, the term "evert" means turning right-side-in, i.e., reversing an inverting process. After the harness 4 is advanced into place, the suction is released and the delivery system 36 is released from the harness 4 and heart 2.

FIGS. 21–25 illustrate the application of the cardiac harness 4 to the heart 2 in various stages. FIG. 21 shows the delivery device, which may be a catheter in one embodiment, comprising a body 46 and a handle 44. The catheter body 46 is advanced through the skin 48 of the patient. The suction 38 moves in proximity to the apex 42 of the heart 2. The harness 4 is inverted (i.e., turned inside out) and is collapsed within the body 46 of the delivery device.

FIG. 22 illustrates engagement of the apex 42 of the heart 2 by the suction cup 38. Suction may be applied to the apex 42 of the heart 2 by moving the handle 44 in one or more directions, or by using a syringe or other suction device (not illustrated).

Figure 23:
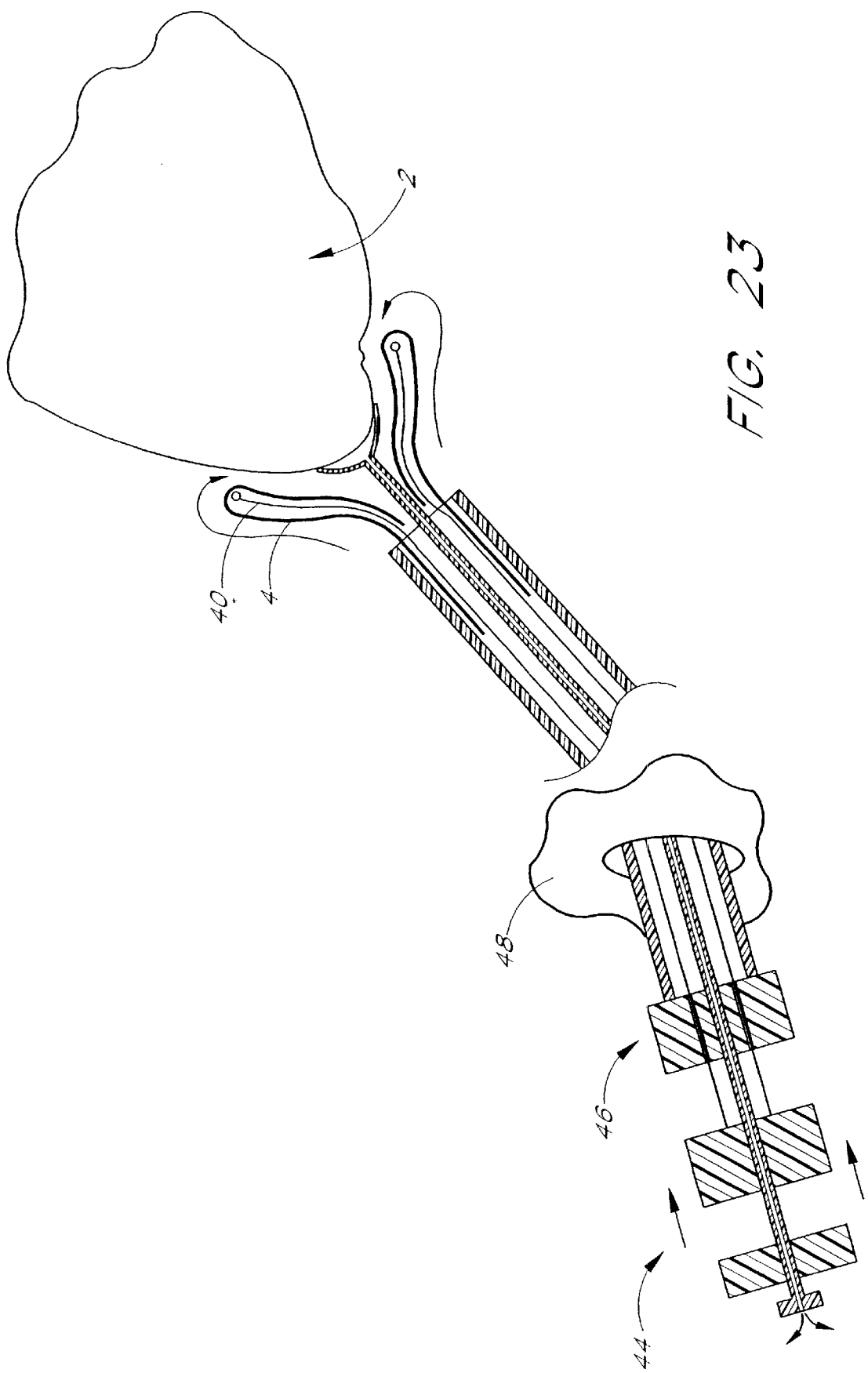

FIG. 23 shows advancement of the harness 4 by the actuating fingers 40 within the body 46 of the delivery device. The harness 4 may be advanced over the heart 2 by moving the handle 44 toward the heart 2 relative to the body 46 of the delivery device.

Figure 24:
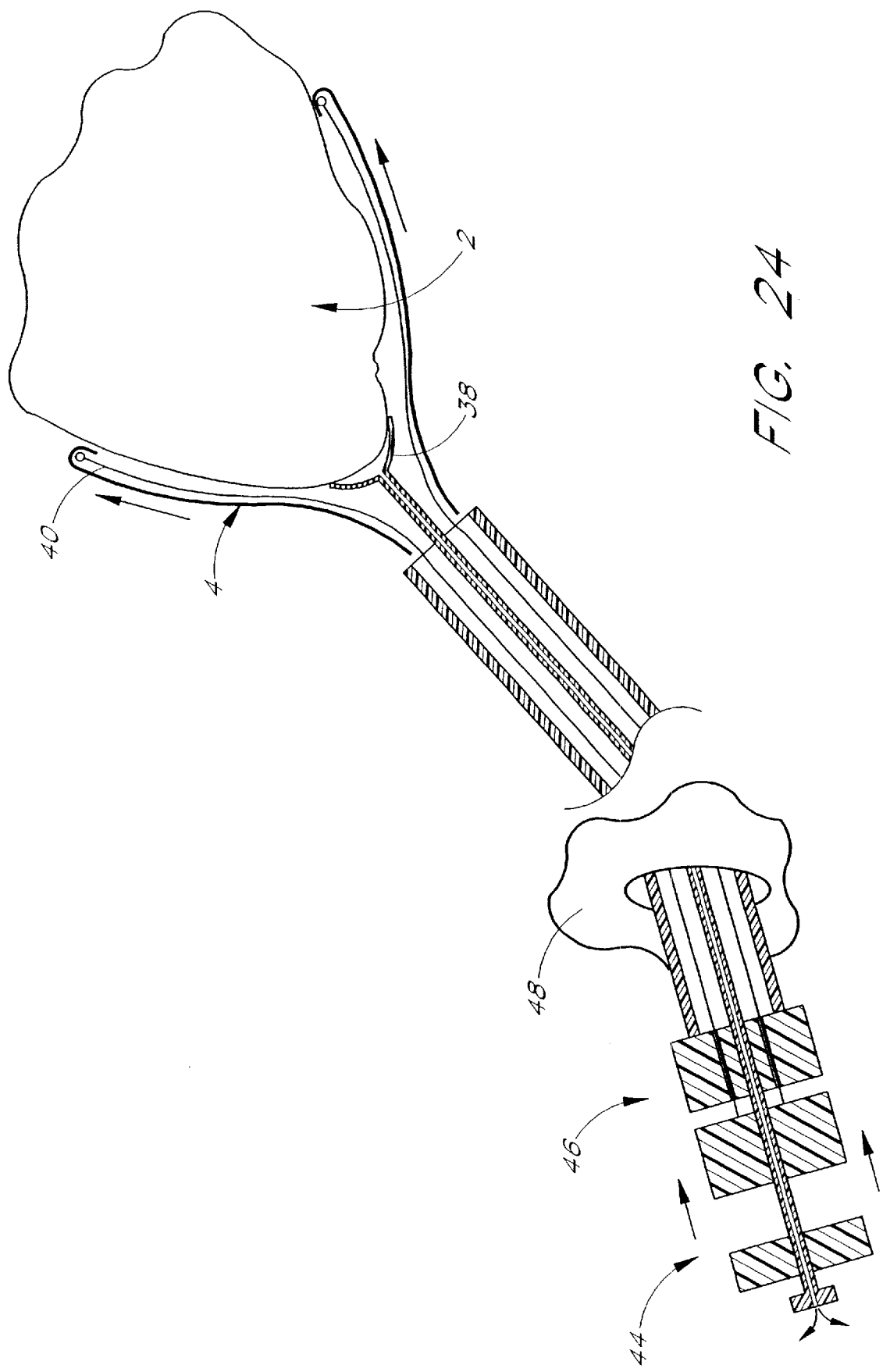

FIG. 24 shows further advancement and unrolling, or everting, of the harness 4 as the actuating fingers 40 move distally and outwardly relative to the delivery device body 46. The suction cup 38 remains engaged on the heart 2.

Figure 25:
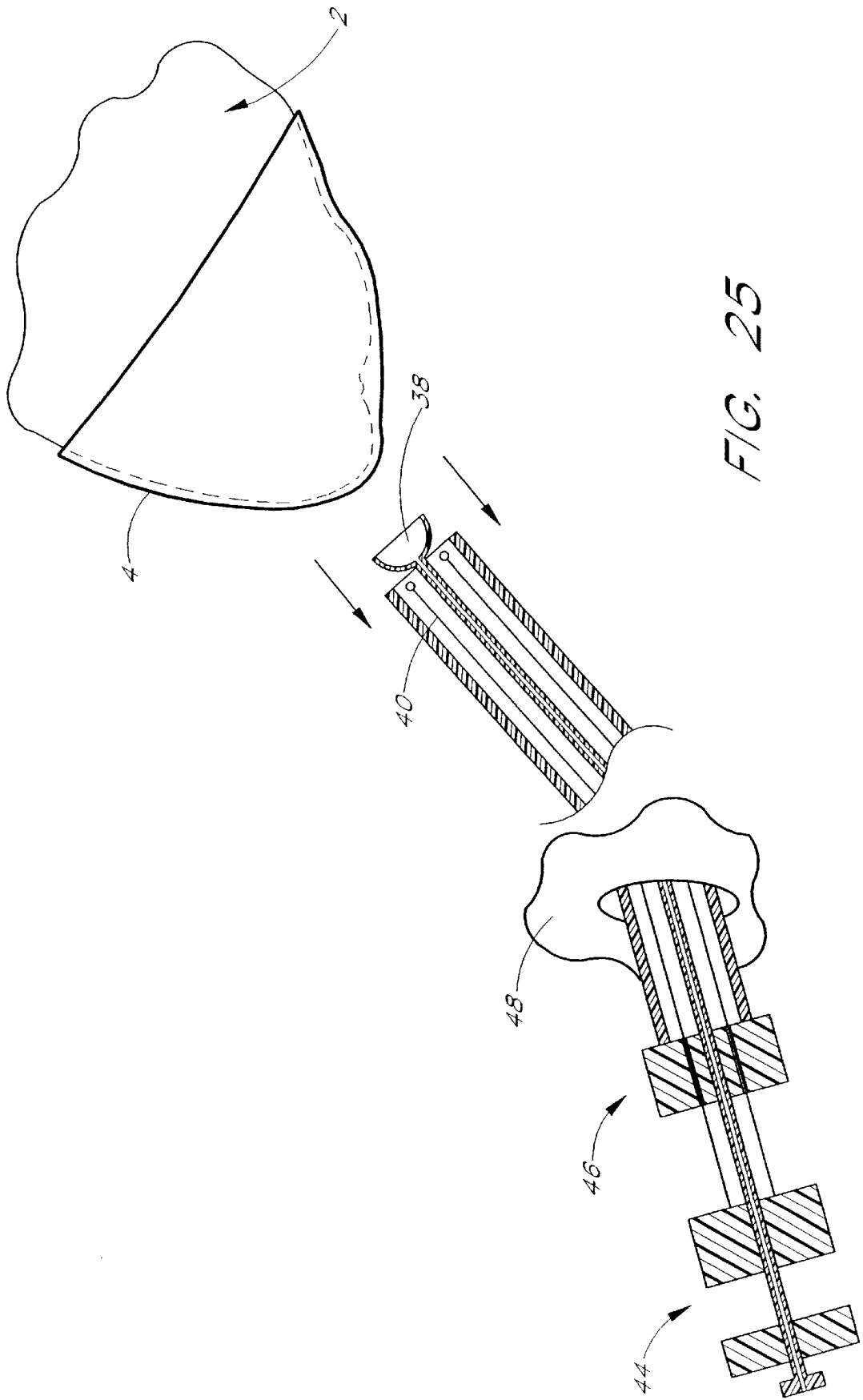

FIG. 25 illustrates completion of the placement of the harness 4 on the heart 2. After the harness 4 is in position on the heart 2, the handle 44 may be withdrawn from the body 46 of the delivery device, pulling the actuating finger 40 back within the body 46 of the delivery device. The suction cup 38 is also released from the heart 2 and harness 4, and the delivery device is withdrawn from the patient through the skin 48.

Figure 26A:
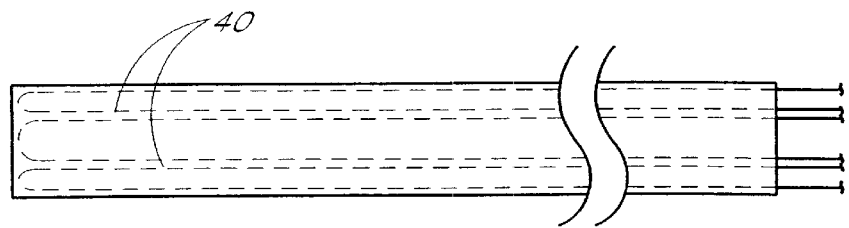
FIGS. 26A–26D are schematic illustrations of a "flower petal" embodiment of the cardiac delivery device.
Figure 26B:
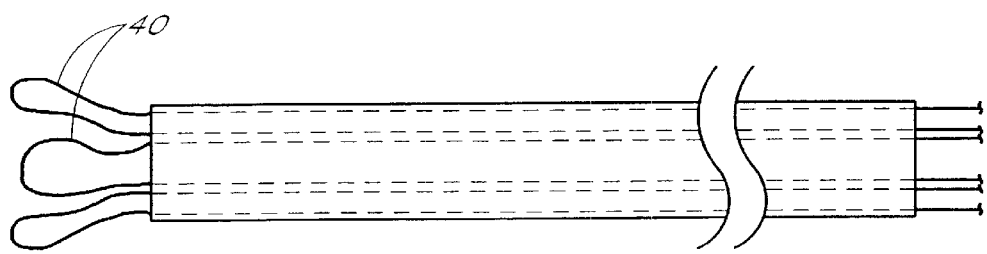
Figure 26C:
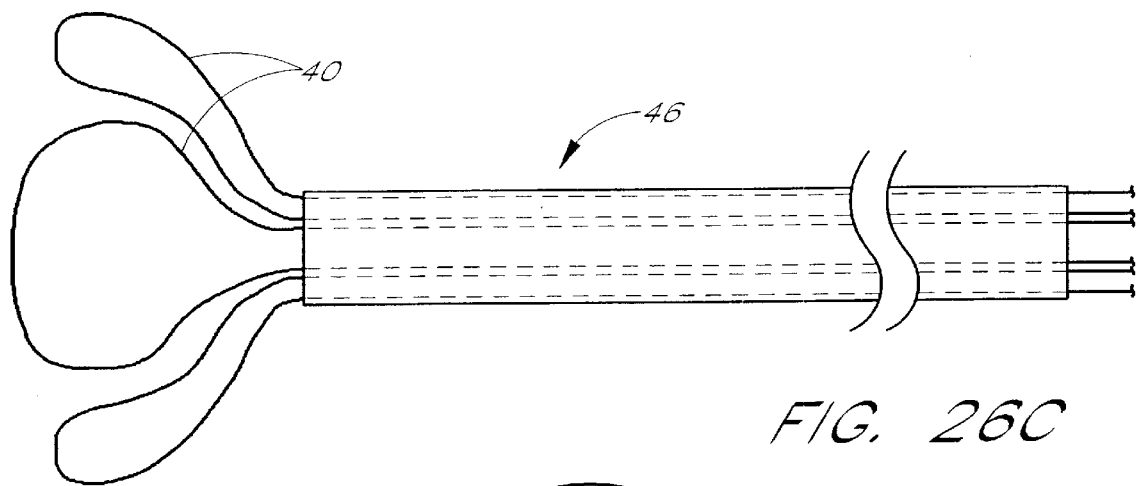
Figure 26D:
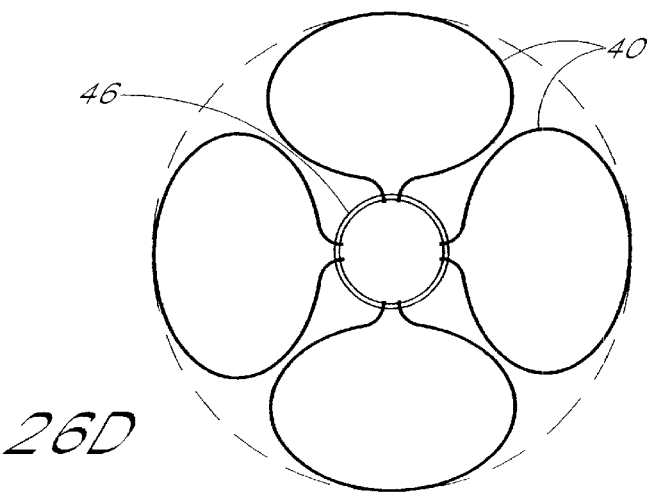

FIGS. 26a–26d illustrate another embodiment of the delivery device, in which the actuating fingers 40 of the device form a loop or "flower petal" configuration. The actuating fingers 40 are withdrawn within the body 46 of the delivery device in FIG. 26a. FIGS. 26b and 26c show a progressive advancement of the actuating fingers 40 distally from the body 46 of the delivery device. As the fingers 40 advance, they expand outwardly into a larger loop or flower petal configuration. FIG. 26d is an en face view of the delivery device body 46 and the flower-petal-shaped actuating fingers 40.

Figure 27A:
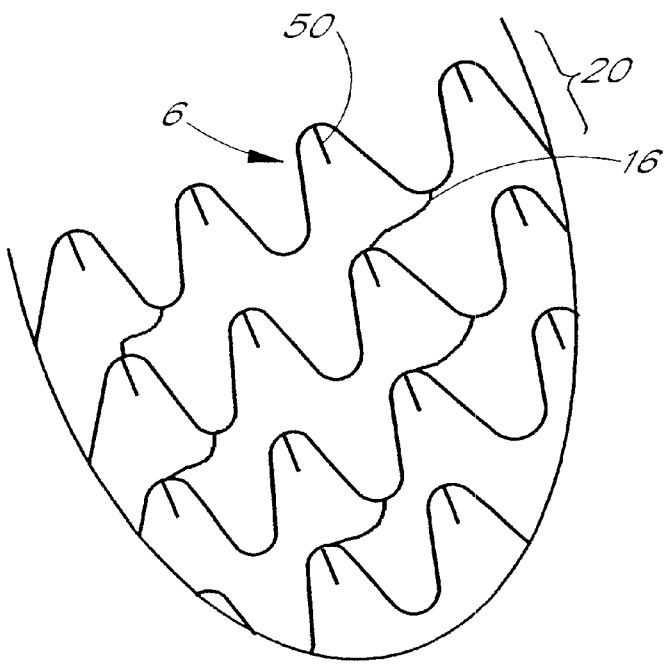
FIGS. 27A–27B are schematic illustrations of sharp anchors extending from the bending hinges of the cardiac harness into the myocardium (heart muscle).
Figure 27B:
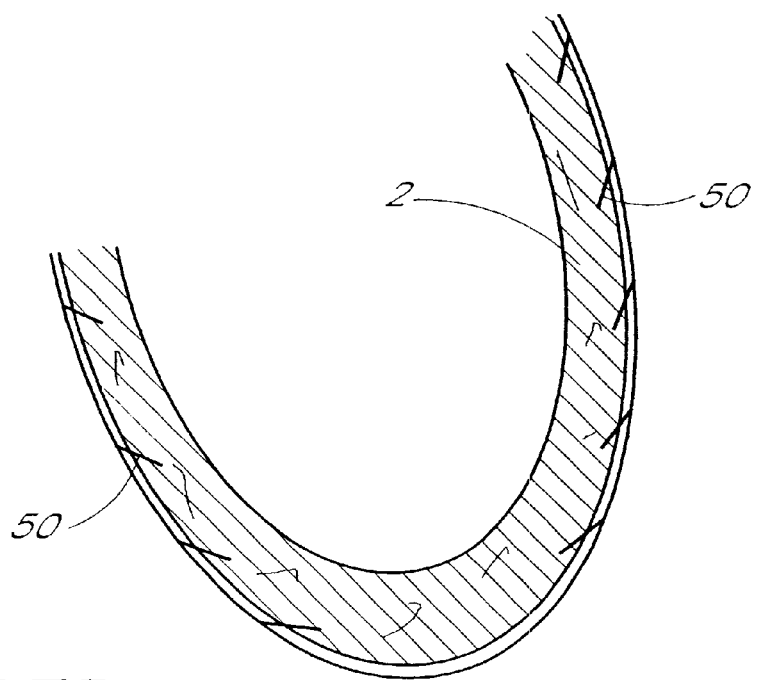

The harness 4 can be secured in place on the heart 2, using sutures or staples to prevent it from migrating. Alternatively, the harness 4 can self-anchor to the epicardium to prevent it from migrating. This self-anchoring can be accomplished by incorporating inward-facing barbs or anchors 50 in the harness structure 4, as illustrated in FIGS. 27a and 27b. The anchors 50 preferably extend from the hinges 6 into the wall of the heart 2.

Figure 28:
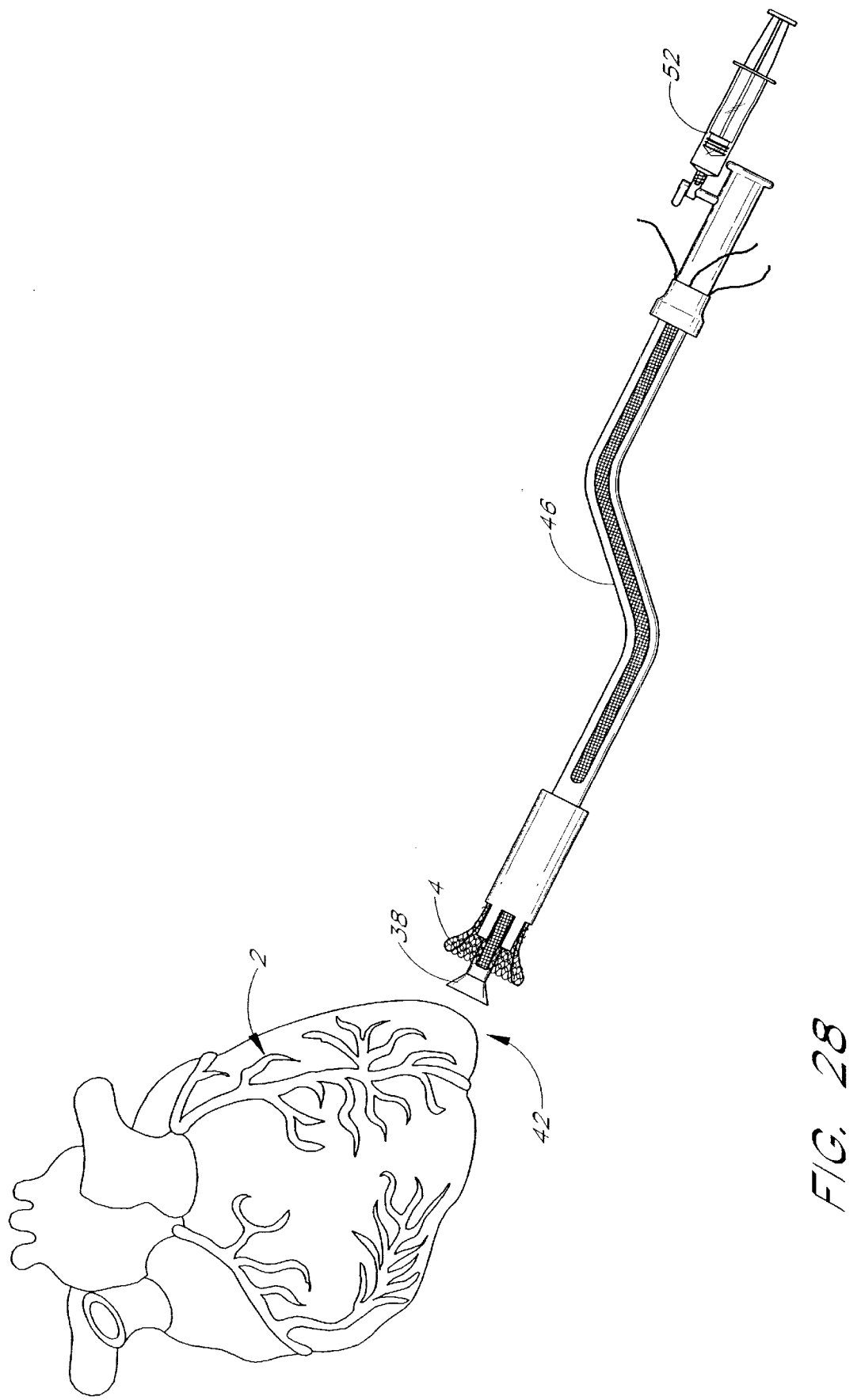
FIG. 28 is a side view illustration of a bent-body embodiment of the cardiac delivery device, proximate to a human heart.

FIG. 28 shows an alternative embodiment of the delivery device. The body 46 of the delivery device is curved to facilitate placement and/or manipulation of the device by the surgeon. Also illustrated is a syringe 52 for injecting fluids or for generating suction on the distal suction cup 38 to secure the suction cup 38 to the apex 42 of the heart 2. Also illustrated is the harness 4 that is partially withdrawn within the body 46 of the delivery device.

Figure 29:
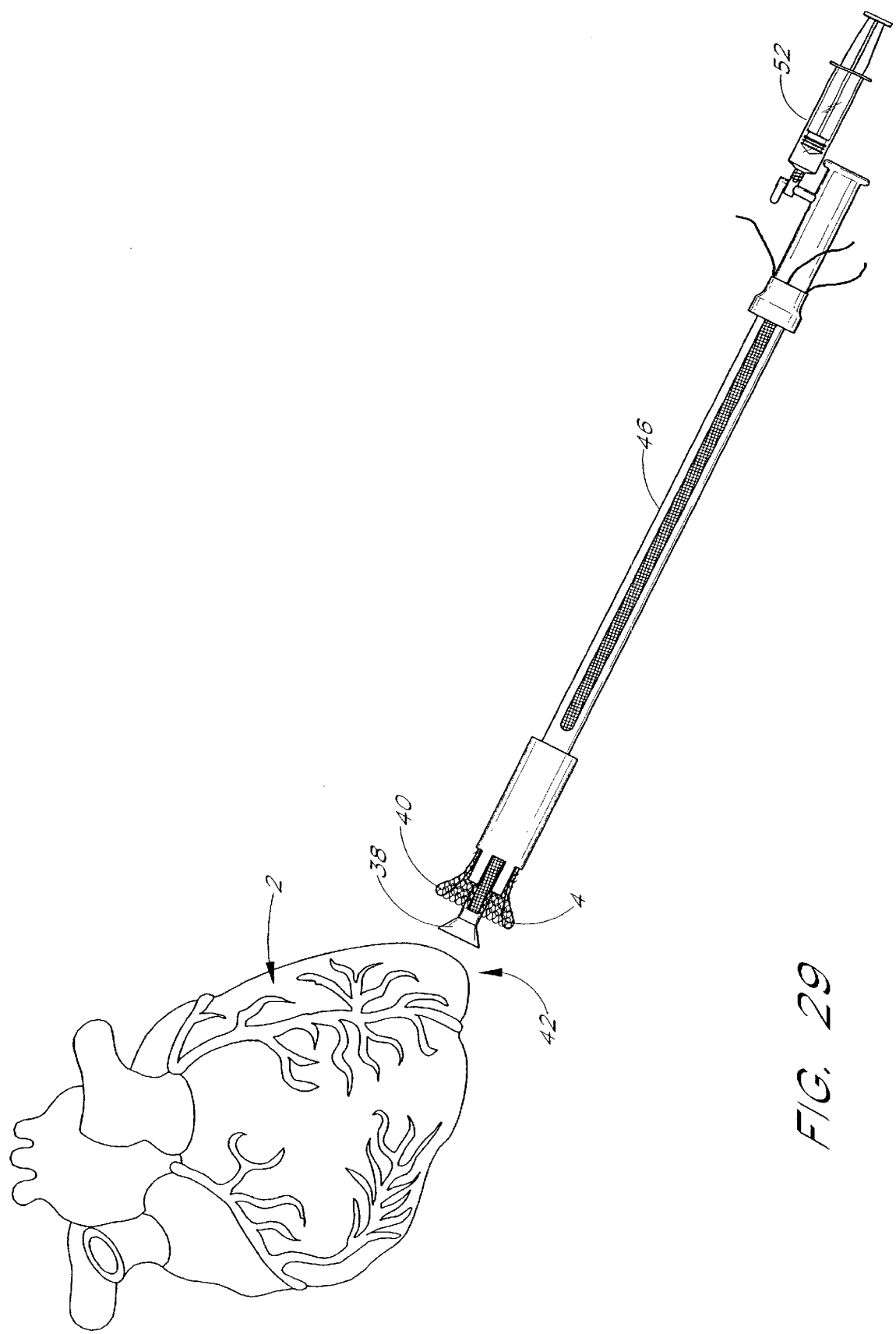
FIG. 29 is a side view illustration of a straight-body embodiment of the cardiac delivery device, proximate to a human heart.

FIG. 29 shows an alternative embodiment of the delivery device. The body 46 of the delivery device is straight in this embodiment.

Figure 30:
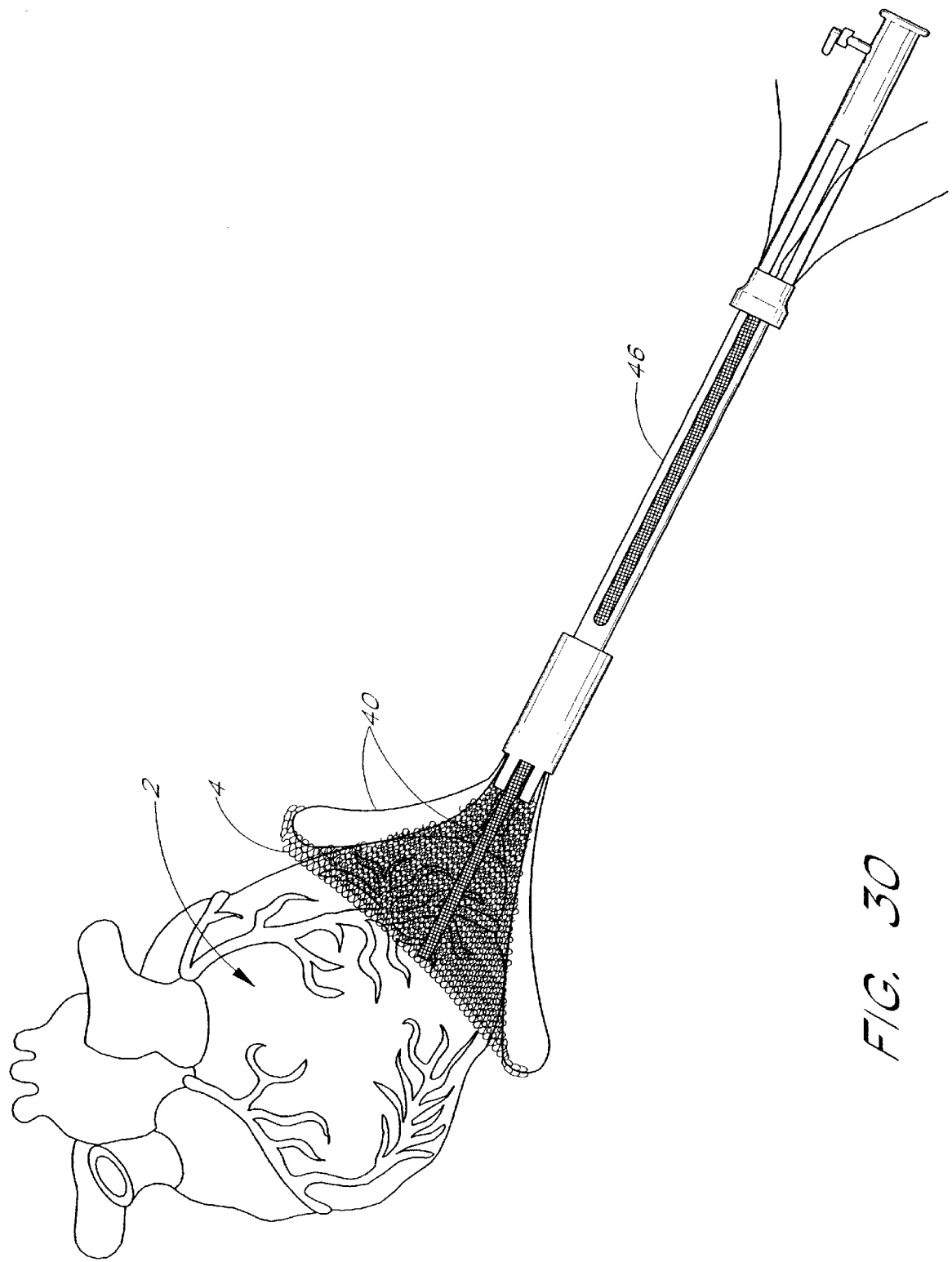
FIGS. 30–31 show progressive steps in the placement of the cardiac harness on a human heart, utilizing the cardiac delivery device.

FIG. 30 illustrates advancement of the harness 4 and actuating fingers 40 onto the heart 2.

Figure 31:
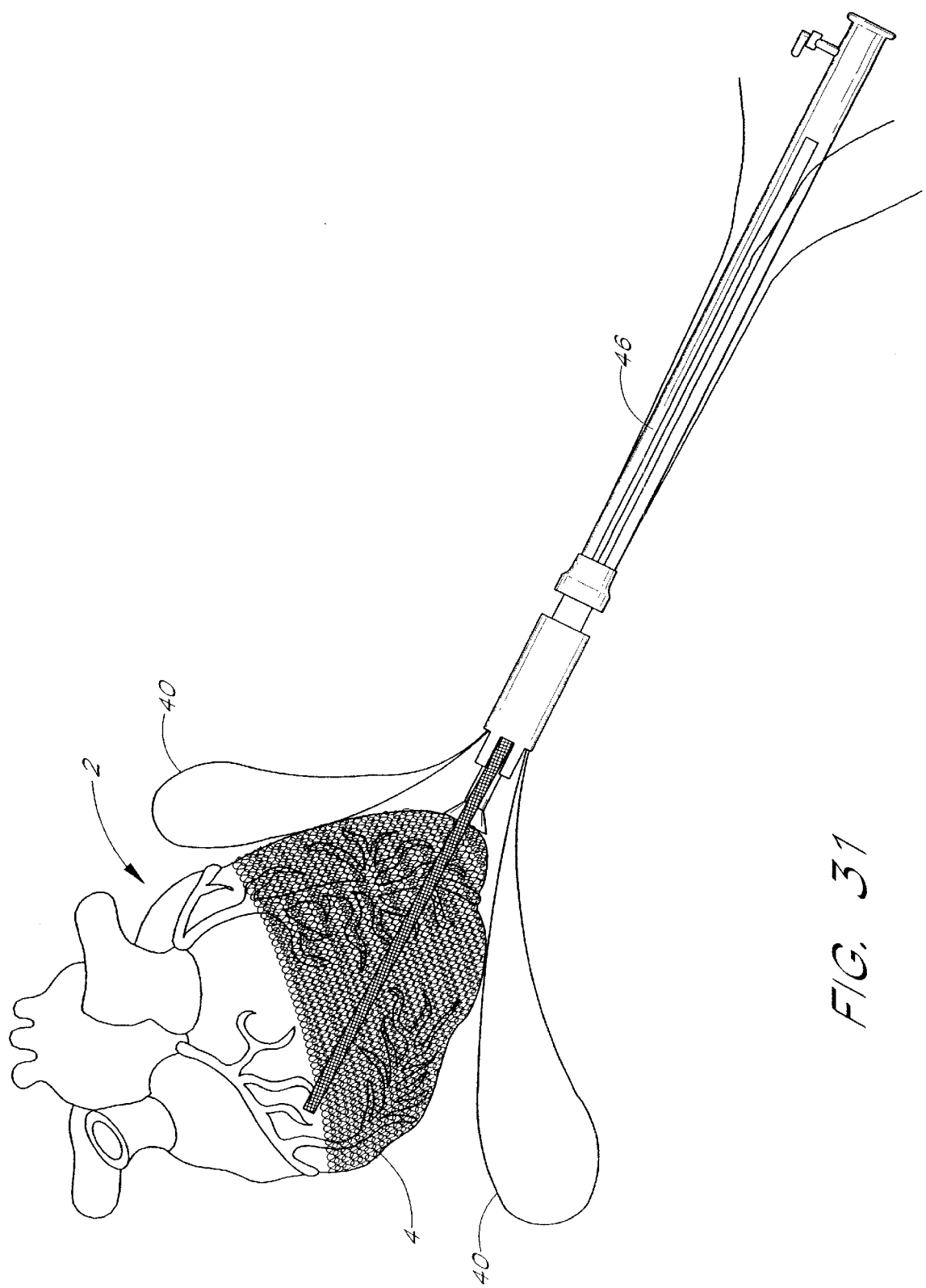

FIG. 31 shows completed placement of the harness 4 onto the heart 2 by the delivery device. Note that the actuating fingers 40 form a loop, and, in some embodiments, the actuating fingers 40 are made of flexible material to form flexible straps or bands.

The harness 4 not only has the capability of acting as a passive restraint around the heart, but may also be actively powered to provide contractile assistance during systole. This may be done by the application of electrical or mechanical power to the harness 4.

If electrical current or heat is applied to the harness 4 in the stressed state, the resistive force generated by the bending deformation increases. In essence, the harness 4 generates a contractile force when current is applied to the harness 4. Hence, it is possible to actively power an otherwise passive elastic harness 4 in order to achieve systolic pumping assistance. This effect is additive in the myocardial sparing benefit that the harness 4 provides.

Figure 32:
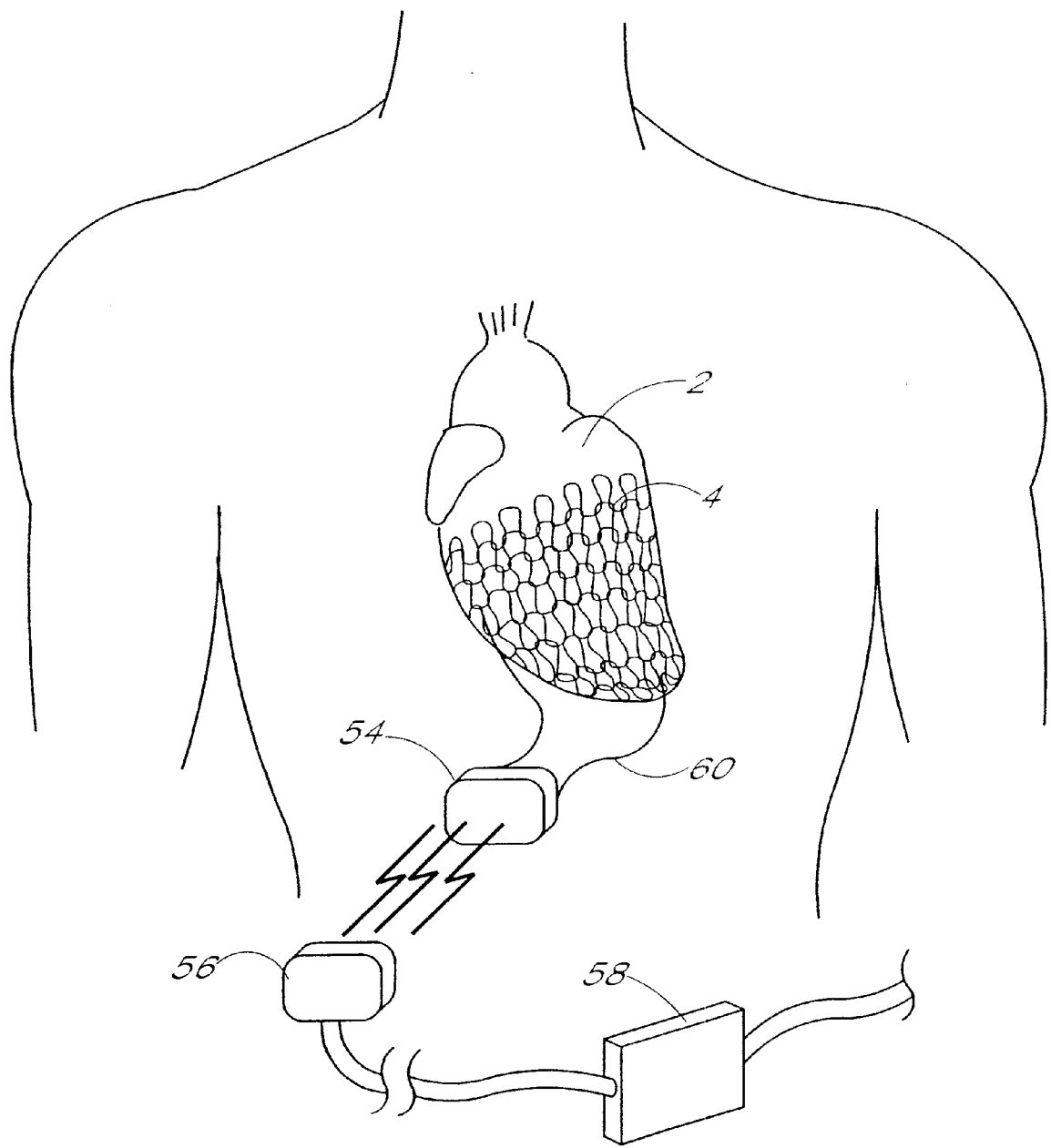
FIG. 32 is a schematic illustration of a cardiac harness applied to the human heart, with direct application of electrical current to the cardiac harness.

During systole and perhaps at end-diastole, current can be applied to the harness 4 to make it contract and thus assist in left ventricular contraction. Such a mechanism is illustrated in FIG. 32. The harness 4 surrounds the heart 2. An electrical wire 60 extends from an internal power supply 54 to the harness 4.

In this context, the internal power supply 54 is a device that supplies electrical energy to the harness 4. It may also comprise a battery and, in some embodiments, a radiofrequency transducer for receiving and/or transmitting radiofrequency signals to and from an external radiofrequency ("RF") transducer 56 which may send and/or receive RF signals from the internal power supply 54. Thus, the external RF transducer 56 may recharge a battery within the internal power supply 54. Also, the external RF transducer 56 may be used to send program information from the external RF transducer 56 to the internal power supply 54, or vice versa, regarding electromechanical sensing and/or pacing information, cardiac rhythm, degree of ventricular or harness contractility, heart-rate information, or the like. Alternatively, the external RF transducer 56 may supply electrical power through inductive field coupling between the external RF transducer 56 and the internal power supply 54.

In some embodiments, an external power supply 58 can be used, which may be a battery pack in various preferred arrangements. The external power supply 58 may supply current to the external RF transducer 56, which may in turn supply electrical energy to the internal power supply 54 through inductive field coupling. The technology for this inductive field coupling, including electronic programming and power transmission through RF inductive coupling, has been developed and is employed in, for example, cardiac pacemakers, automatic internal cardiac defibrillators, deep brain stimulators, and left ventricular assist devices.

The power requirement of the device of the disclosed embodiments is significantly lower than that of conventional left ventricular assist device because the native heart in the present application continues to do some work. The powered harness 4 merely augments native cardiac contractions.

Rather than a Nitinol harness 4 providing active systolic assistance, variable current can be applied to the Nitinol to simply vary the harness's 4 passive stiffness. As such, power is not used to actively "squeeze" the heart 2 during systole. The harness 4 is instead a passive elastic harness with adjustable compliance. A physician can adjust the power to a harness 4 to vary the amount of resistive pressure it exerts on the left ventricle during both systole and diastole. The passive stiffness of the harness 4 can be set to change throughout the cardiac cycle, or it can be adjusted to maintain constant levels. For example, when the cardiac harness 4 is placed on the heart 2, the physician can set the harness 4 to a certain degree of stiffness. Depending on how the patient responds, the physician can then increase or decrease stiffness by varying the electrical stimulating parameters to the harness 4. Adjustment and stimulation of the harness 4 can be accomplished through an implantable pacemaker-like box, the internal power supply 54, that is electrically connected to the harness 4 through at least one wire 60. This is one embodiment of the configuration illustrated in FIG. 32.

The harness 4 may be integrated with an implantable pacemaker or a internal cardiac defibrillator, according to the needs of the patient.

Figure 33:
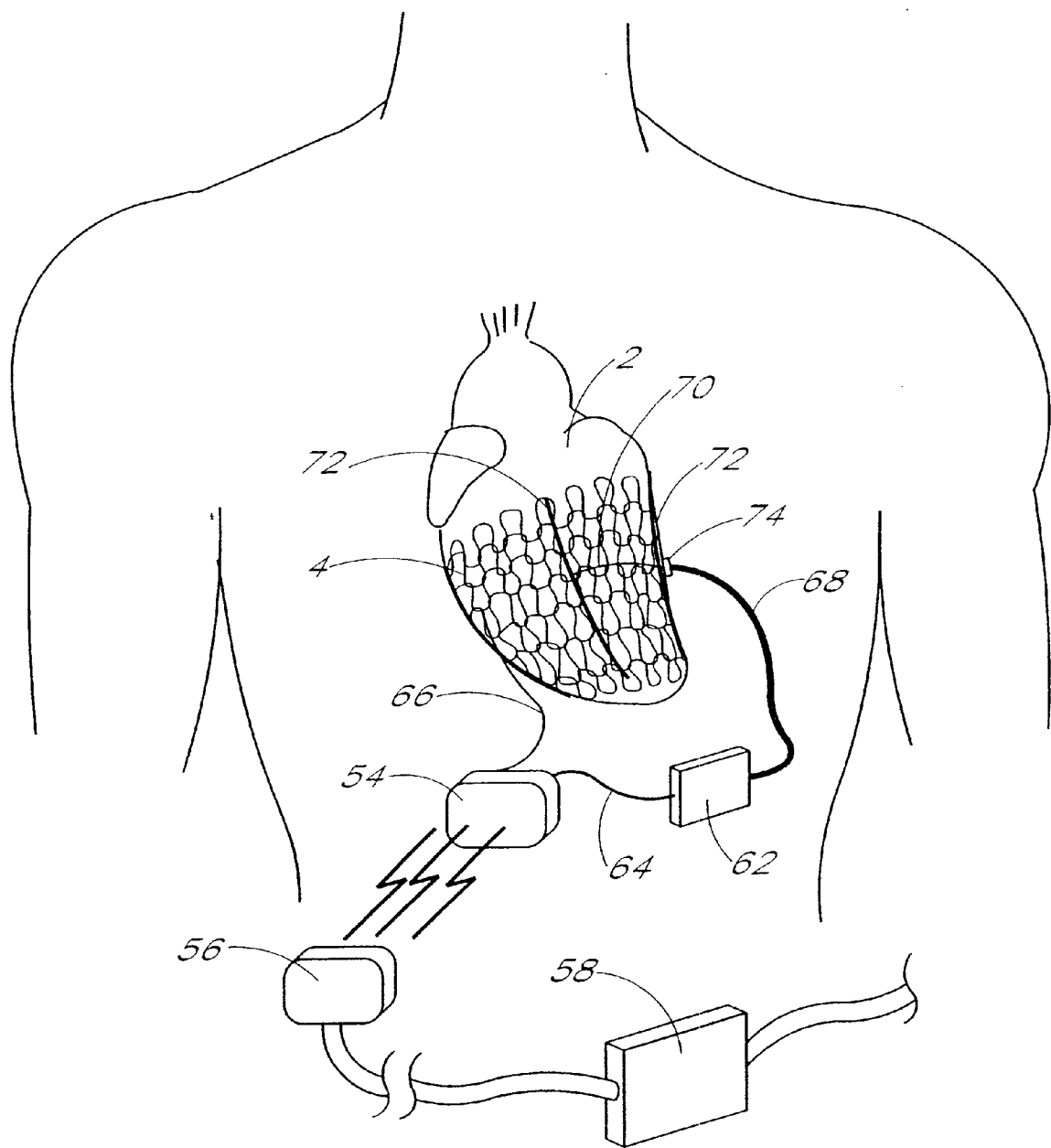
FIGS. 33–34 are schematic illustrations of the cardiac harness in place on the human heart, together with an actuating device and cable for application of mechanical force to the cardiac harness.
Figure 34:
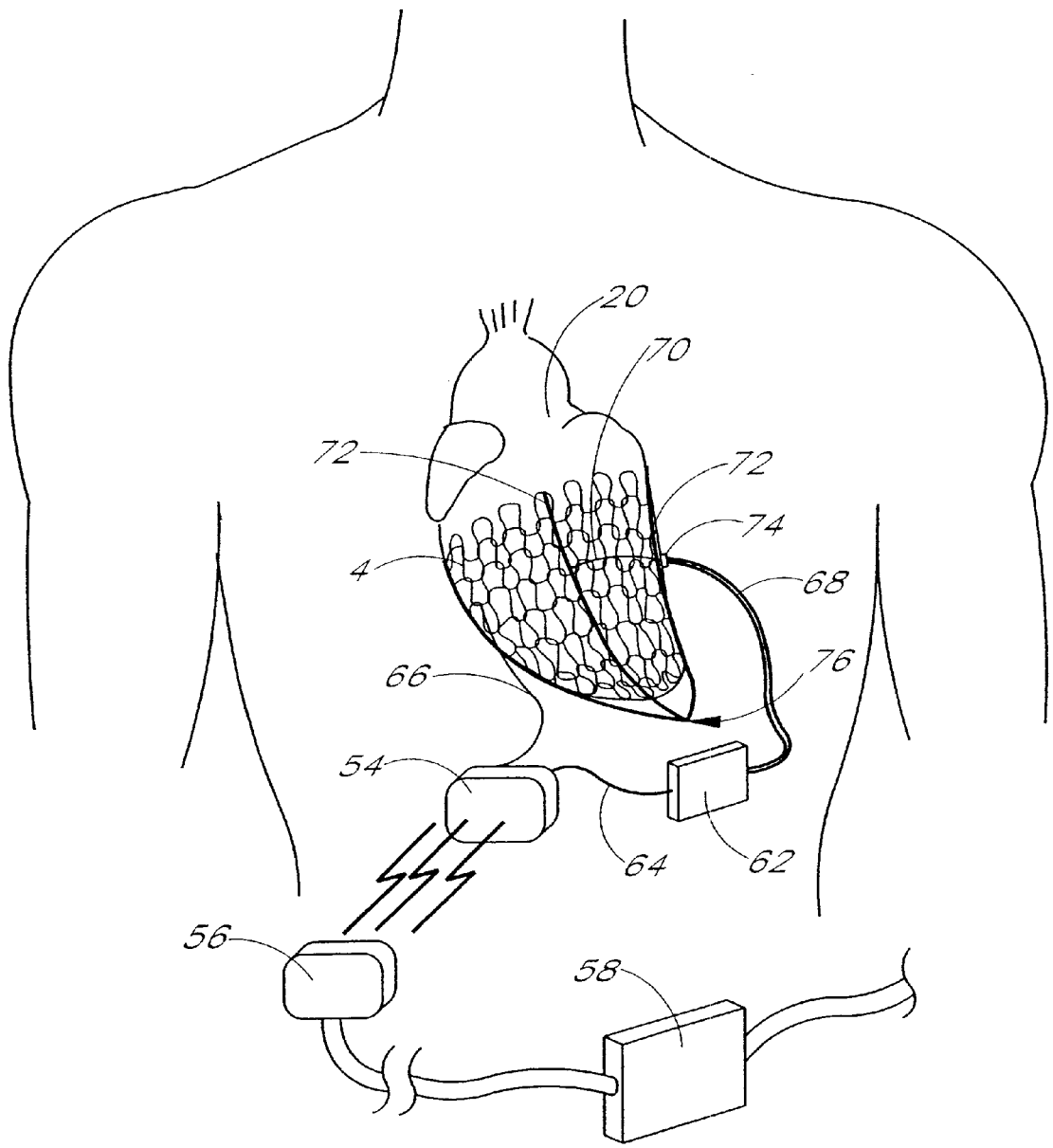

Mechanical power can be applied to the harness 4 through sliding cables 70 as illustrated in FIGS. 33 and 34. A cable 70 can extend over the surface of the harness 4 between two points. The cable 70 is actually an inner sliding element that resides partially within an outer housing 68. Mechanical actuation of the cable 70 by, for example, an actuation box 62 causes the two components, illustrated in FIGS. 33 and 34 as struts 72 within the harness 4, to slide or otherwise move relative to each other. If the end 74 of the housing 68 is attached to one strut 72, and the distal end of the cable 70 is attached to another strut 72, then actuation of the cable causes the two struts to move closer and/or farther apart relative to one another, causing the heart to contract and/or expand. If timed with systole, this mechanism provides contractile assistance.

Also illustrated in FIGS. 33 and 34 are the actuation box 62, which converts electrical energy to mechanical energy to move the cable 70 within the housing 68; a power lead line 64, extending from the internal power supply 54 to the actuation box 62; and an electrical sensing lead 66, which can sense cardiac contractions or cardiac electrical activity, such as an electrocardiographic signal. This sensing is similar to the way in which pacemakers sense cardiac electrical activity, receiving information concerning the rate and rhythm of the heartbeat. Also illustrated in FIGS. 33 and 34 are the external RF transducer 56 and the external power supply 58, as previously described.

FIG. 33 illustrates the struts 72 as unattached to one another, while FIG. 34 shows the struts 72 attached at a point 76 near the apex of the heart 2. These two different embodiments can confer different mechanical and hemodynamic advantages upon actuation of the cable 70 and consequent contraction and expansion of the heart 2.

FIGS. 35a–36b illustrate a method of manufacturing the strips, or rows, of hinges 6. A sheet (or more than one sheet) of Nitinol or other suitable material is cut to form a single, continuous ring 80 of hinges 6. This ring 80 is initially flat after it has been cut from the sheet of material, as shown in FIG. 35a (top view) and 35b (side view). The ring 80 is preferably parallel to the surface (e.g., a table or board) on which the ring 80 is formed. The ring is then manipulated to create a band-like configuration, which can be cylindrical or beveled, as illustrated in FIG. 36a (top view) and 36b (side view).

Compared to conventional left ventricular assist devices, the harness 4 of the disclosed embodiments has many advantages. It can be minimally invasively delivered, and it can be permanently implanted without need for subsequent removal. This allows it to provide incremental therapy as needed. If necessary, it can be powered to provide contractile assistance. If this is not necessary, the power can be shut off to allow it to act as a passive elastic reinforcement for the failing heart.

In addition, such a system can provide circulatory assistance with a fraction of the power demands of a left ventricular assist device. Left ventricular assist devices are estimated to require nearly ten watts of power. The heart itself operates at only approximately one watt of power. Because a powered harness works with the existing heart, it should not need nearly the amount of power of a left ventricular assist device. In addition, because the harness 4 does not come in direct contact with blood, there is no need to anticoagulate the patient with, for example, warfarin (Coumadin) or heparin. There is also no independent reason to treat the patient with antiplatelet drugs. A harness system involves less machinery than a left ventricular assist device. This and other attributes impose less detriment to a patient's quality of life. Last, such a system is relatively simple and therefore less costly than a left ventricular assist device.

Power to actuate the cable 70 can come from an internal or external source. An internal source can alternatively be skeletal muscle, such as in situ latissimus dorsi muscle or a mechanical motor. If power is needed, it can be delivered transcutaneously as described above, using existing technology developed by, for example, left-ventricular-assist device companies.

Although the present invention has been described in terms of certain preferred embodiments, other embodiments that are apparent to those of ordinary skill in the art are also within the scope of the invention. Accordingly, the scope of the invention is intended to be defined only by reference to the appended claims.

What is claimed is:

1. A method, comprising;
   providing a cardiac harness sized and configured to fit around at least a ventricle of a patient's heart;
   providing at least one pad having in a marginal edge;
   arranging the pad marginal edge in proximity to but not impinging upon a coronary artery; and
   placing the cardiac harness on the heart so that the harness extends over the pad and coronary artery.

2. The method of claim 1, wherein arranging the pad marginal edge comprises aligning the marginal edge with a substantial portion of the length of the coronary artery.

3. The method of claim 1, wherein the coronary artery is selected from the group consisting of the left anterior descending artery, the right coronary artery, the left circumflex artery, the posterior descending artery, and the obtuse marginal artery.

4. The method of claim 1, wherein the cardiac harness comprises an elastic band configured to impart a compressive force on the heart, and the pad is arranged to reduce compression of said artery by said harness.

5. The method of claim 4, wherein the cardiac harness comprises interconnected strands of material.

6. The method of claim 1, additionally comprising providing a second pad having a marginal edge, and arranging the second pad on an opposite side of the coronary artery from the first pad.

7. The method of claim 6, wherein the first and second pads are arranged so that their marginal edges are generally parallel to the coronary artery.

8. A method, comprising:

providing a cardiac harness sized and configured to fit around at least a ventricle of a patient's heart, the harness comprising a slot formed therein; and arranging the cardiac harness on the heart so that the slot is generally aligned with a substantial portion of the length of at least one coronary artery selected from the group consisting of the left anterior descending artery, the right coronary artery, the left circumflex artery, the posterior descending artery, and the obtuse marginal artery.

9. The method of claim 8, wherein the slot is defined by a frame integrated into the harness.

10. The method of claim 9, wherein the frame comprises a wire frame.

11. The method of claim 9, wherein the harness comprises strands of material, and the strands are suspended from the wire frame.

12. The method of claim 11, wherein each of the strands comprises at least one spring element.

13. The method of claim 8, wherein the harness is substantially unitarily formed.

* * * * *